United States Patent [19]

Hideg et al.

[11] Patent Number: 5,032,600
[45] Date of Patent: Jul. 16, 1991

[54] ALKYL DIAMINE DERIVATIVES

[75] Inventors: Kalman Hideg; Olga H. Hankovszky, both of Pecs; Laszlo Frank, Tiszavasvari; Ilona Bodi, Tiszavasvari; Jozsef Csak, Tiszavasvari, all of Hungary

[73] Assignee: Alkaloida Vegyeszeti Gyar, Tiszavasvari, Hungary

[21] Appl. No.: 607,165

[22] Filed: Oct. 31, 1990

Related U.S. Application Data

[62] Division of Ser. No. 441,370, Nov. 27, 1989, which is a division of Ser. No. 109,819, Oct. 16, 1987, Pat. No. 4,897,413, which is a division of Ser. No. 662,298, Sep. 20, 1984, Pat. No. 4,703,056.

[30] Foreign Application Priority Data

| Jan. 21, 1983 | [HU] | Hungary | 191/183 |
| Feb. 4, 1983 | [HU] | Hungary | 384/83 |
| Feb. 4, 1983 | [HU] | Hungary | 385/83 |
| Feb. 4, 1983 | [HU] | Hungary | 386/83 |

[51] Int. Cl.$^5$ .................. A61K 31/44; A61K 31/40
[52] U.S. Cl. .................. 514/343; 514/422; 514/423; 544/284; 544/287; 546/115; 546/281; 548/465; 548/526; 548/527; 548/537; 548/565
[58] Field of Search .............. 546/281; 548/527, 537; 514/343, 422, 423

[56] References Cited

U.S. PATENT DOCUMENTS

| 4,452,989 | 6/1984 | Deckner et al. | 548/537 |
| 4,643,758 | 2/1987 | Burow, Jr. et al. | 548/537 |
| 4,731,376 | 3/1988 | Hideg et al. | 548/537 |
| 4,933,354 | 6/1990 | Ikeguchi et al. | 546/281 |

Primary Examiner—C. Warren Ivy
Assistant Examiner—James H. Turnipseed
Attorney, Agent, or Firm—Herbert Dubno; Jonathan Myers

[57] ABSTRACT

The invention refers to new diamines of the Formula I

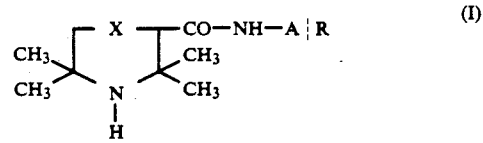

wherein
R stands for

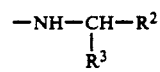

or —NH—COA$^1$—R$^4$ or

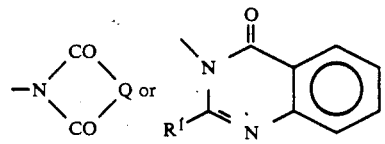

wherein
A stands for C$_{1-5}$ alkylene which can be substituted by hydroxyl,
X stands for a single or double bond,
R$^2$ stands for aryl or heteroaryl optionally substituted by halogen, C$_{1-4}$ alkoxy or acylamino,
R$^3$ stands for hydrogen or C$_{1-4}$ alkyl,
A$^1$ stands for a single bond or C$_{1-5}$ alkyl optionally substituted by hydroxyl or thioalkylene or oxyalkylene,
R$^4$ stands for a 5- or 6- membered aromatic or heteroaromatic ring which can be substituted by one or more hydroxyl, C$_{1-4}$ alkyl and/or C$_{1-4}$ alkoxy and/or halogen or methylenedioxy and the alkyl group can be unsaturated as well,
Q stands for a 6-membered ring which can be partially hydrogenated, and
R$^1$ stands for C$_{1-4}$ alkyl.

The new compounds are antiarrhythmic agents.

3 Claims, No Drawings

ALKYL DIAMINE DERIVATIVES

CROSS REFERENCE TO RELATED APPLICATION

This is a divisional of co-pending application Ser. No. 07/441,370 filed on Nov. 27, 1989 which is a divisional of Ser. No. 07/109,819 filed Oct. 16, 1987 now U.S. Pat. No. 4,897,413, which is a divisional of Ser. No. 06/662,298 filed Sept. 20, 1984, now U.S. Pat. No. 4,703,056.

The present invention relates to alkyl diamine derivatives, a process for the preparation thereof and pharmaceutical compositions containing same.

In the patent specification hereinafter in the formulae the substituents are defined as follows:

R stands for

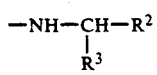

or —NH—COA$^1$—R$^4$ or

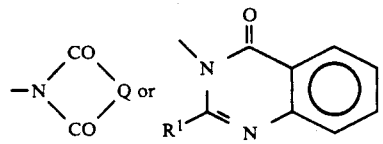

wherein
A stands for C$_{1-5}$ alkylene which can be substituted by hydroxyl,
X stands for a single chemical bond or a double bond,
R$^2$ stands for an aryl or heteroaryl group optionally substituted by halogen, C$_{1-4}$ alkoxy or acylamino,
R$^3$ stands for hydrogen or C$_{1-4}$ alkyl,
A$^1$ stands for a single chemical bond or a C$_{1-5}$ alkylene optionally substituted by hydroxyl or thioalkylene or oxyalkylene,
R$^4$ stands for a 5- or 6-membered aromatic or heteroaromatic ring which can be substituted by one or more hydroxyl, C$_{1-4}$ alkyl and/or C$_{1-4}$ alkoxy and/or halogen or methylenedioxy, and the alkyl group can be unsaturated as well
Q stands for a 6-membered ring, which can be partially saturated and
R$^1$ stands for C$_{1-4}$ alkyl,
Q$^1$ stands for halogen, O-alkyl or an active ester moiety.

The present invention refers to compounds of the Formula I

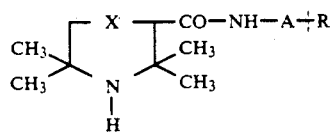

salts thereof as well as pharmaceutical compositions containing the compounds of the general Formula I.

The compounds have not been disclosed so far in the prior art. The biological activity of the new compounds can be advantageously compared with the generally accepted antiarrhythmic agents such as quinidine, and procaine amide. In fact in some cases the activity is several times higher than the activity of said known anti-arrhythmic agents and the toxicity thereof is less than one tenth of the therapeutic dose.

The amines and salts of the Formula I prepared according to the invention can be formulated to pharmaceutical compositions by admixing the active ingredients with the conventionally used excipients, such as carriers, lubricating agents and diluents. The pharmaceutical compositions can be administered in the form of parenteral, enteral and peroral compositions.

The antiarrhythmic activity of the compounds of the Formula I was compared in a preventive aconitine arrhythmia test on rats as follows:

Male and female
rats of Wistar strain weighing 200 to 250 g. were narcotized i.p. with 1.25 g./kg. of urethane and their ECG was registered by a Hellige equipment by II standard limb head.

Arrhythmia was induced by an i.v. infusion of 30 μg/kg. aconitine nitrate whereafter the ECG was continuously monitored for 30 minutes.

The test substances were always administered to the animals 2 minutes before giving the aconitine infusion, i.v., at i.v. LD$_{50/10}$ dosis measured in mice.

Those cases were considered positive, where within 30 minutes after the aconitine infusion not a single phase of the arrhythmia occured.

In control animals pretreated i.v. with a 0.9% sodium chloride solution (0.1 ml./100 g.) (n=20) the arrhythmogenic activity of the aconitine nitrate appeared after 2.88±0.32 minutes.

In cases of compounds having outstanding antiarrhythmic activity ED$_{125}$ and ED$_{150}$ values were calculated in arrhythmia test carried out in rats according to Zetler an Strubelt (Arzneim.-Forsch.) Drug. Res. 1980. 30, 1947).

The acute intravenous (i.v.) toxicity values of the test-compounds was determined by the method of Litchfield and Wilcoxon and as test-animals white mice of both sexes were used (J. of Pharmacol. 1949, 96, 99.).

Biological test results obtained for some new diamines according to the invention are summarized in Table II. Per cent values of the positive cases, average time of the appearance of the arrhythmia—when the induced arrhythmia appeared within 30 minutes and toxicity values are shown.

The test results obtained in various arrhythmia tests show that apart from the significant anti-arrhythmia activity of the compound they are also effective from a physiological point of view in ceasing heart arrhythmia.

The antiarrhythmia effectivity sometimes surpasses the activity of the referential substances: quinidine and procainamide several times and at the same time when examined the negative inotrop and negative chronotrop activity of these compounds in vitro on isolated atrium compositions, said activities do not achieve the heart frequency decreasing or contraction power decreasing activity of quinidine.

A further advantage of the compounds of the present invention is that even in the highest used dosis they do not cause ventricular arrhythmia, they do not include pathological bradychardia and almost do not influence the blood pressure of the test animals. Thus the compounds can advantageously be used to prevent or cause heart arrhythmia when administered parenterally or enterally.

The diamines according to the invention can be combined with other heart drugs, blood pressure regulators, tranquilizers, etc.

The new compounds of the Formula according to the invention include compounds which contain as $R^2$ one or more aromatic rings substituted by chlorine, bromine, iodine or fluorine. The aromatic rings can bear one or more $C_{1-4}$ alkoxy groups at any position.

$R^2$ can also stand for a heteroaryl group which can have 5 or 6 members and can contain at any position one or more nitrogen, oxygen and/or sulphur atoms as heteroatom. Substituent $R^2$ can be substituted by acylamino group as well. $C_{2-5}$ aliphatic acyl groups are preferred which can be straight or branched chained and can, if desired, contain further substituents as well.

In the Formula I group A can stand for a $C_{1-4}$ alkylene group which can be substituted by hydroxyl. This alkylene group can be branched. The hydroxyl group or groups can be at any carbon atom.

The present invention also provides a process for the preparation of the compounds of the Formula I and salts thereof.

The compounds of the present invention can be prepared by reacting an amine of the Formula II

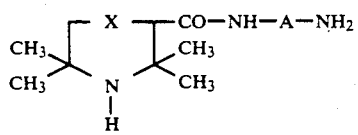 (II)

with the compound of Formula III

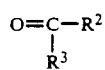 (III)

IV,

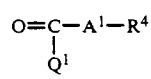 (IV)

VI,

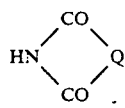 (VI)

or VII,

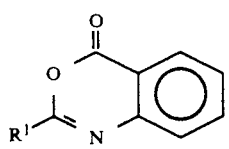 (VII)

depending on the substituents in the end-product. The obtained product is optionally reduced.

The acyl amine of the Formula II used as starting material, can contain a pyrroline or pyrrolidine ring. Accordingly, the acylated product of the invention can also contain a pyrroline or pyrrolidine ring. If the end-product should be a pyrrolidine-containing product so as starting material a pyrrolidine containing compound of the Formula II can be used or the double bond of the pyrroline ring can be saturated in the diacyl amine acylated according to the invention.

When preparing the compound of the Formula IA

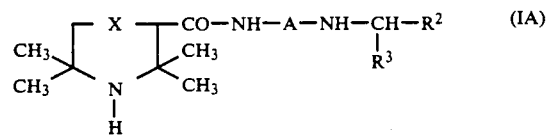 (IA)

falling under the scope of the Formula I, as a first step a Schiff base of the Formula IX

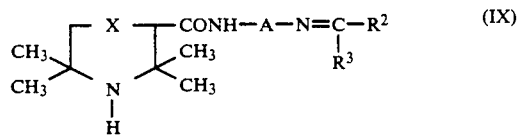 (IX)

is prepared. According to the invention the condensation is preferably carried out in an anhydrous aprotic solvent, preferably in benzene, toluene, xylene or tetrahydrofuran. The condensation can also be performed without any solvent.

The obtained Schiff base is isolated from the reaction mixture or can be reduced without isolation. Depending on the reducing agent diamines of the Formula X

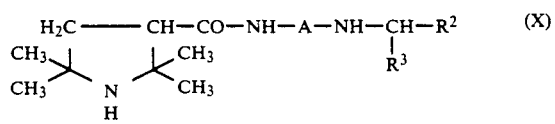 (X)

or XI

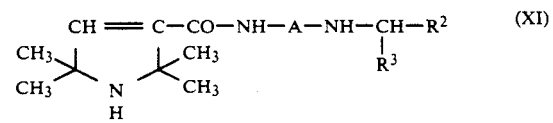 (XI)

falling under the scope of the Formula IA can be prepared. As intermediate products Schiff bases of the Formula XII

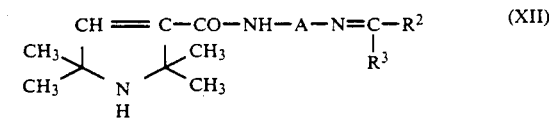 (XII)

or XII

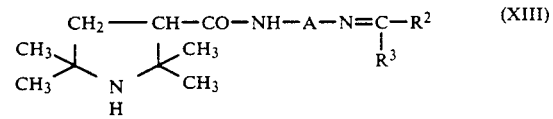 (XIII)

falling within the scope of the Formula IX can be reduced

When preparing diamines of the Formula X one can subject the Schiff base of the Formula XII to hydrogenation in the presence of a catalyst. As catalyst one can preferably use palladium. As a solvent alcohol can be employed As catalyst 5–10% palladium/charcoal catalyst can preferably be used at room temperature and at atmospheric pressure.

Alternatively, when preparing diamines of the Formula X one can use as starting material a Schiff base of the Formula XIII. In this case reduction is conducted with a complex metal hydride. Sodium or potassium borohydride is preferred and the reduction is performed in the presence of an alkanol.

In order to prepare diamines of the Formula XI it is preferred to use a Schiff base of the Formula XII as a starting material. The reduction can be conducted with a complex hydride. Various known complex hydrides can be employed but reduction is preferably carried out with sodium or potassium borohydride. Reduction is preferably conducted in the presence of an alkanol.

The reaction mixture can be processed by different methods e.g. the solvent can be evaporated and the complex decomposed by water thereafter the compound of the Formula I can be extracted with a water immiscible solvent such as ether, benzene, ethylacetate or chloroform.

In order to prepare diamines of the Formula IB

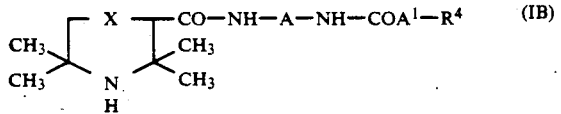

falling within the scope of the Formula I an acyl amine of the Formula II can be reacted with a reactive carboxylic acid derivative suitable to introduce a group of the Formula of —CO—A$^1$—R$^2$ and then in the obtained product the unsaturated bond is optionally reduced and/or if desired, a salt is formed with an organic or inorganic acid residue.

For the acylation as reactive carboxylic acid derivatives carboxylic acid halides, preferably chlorides, bromides can be employed. Other active carboxylic acid derivatives are also suitable for acylation, such as acid esters or active esters. Thus chloroformic acid ethyl ester, pentahalogen phenyl ester or carboxylic acid succinimide esters etc. containing —A$^1$—R$^2$ group can preferably be used.

If the acylation is performed with carboxylic acid halides the reaction is preferably performed in an anhydrous aprotic solvent. As solvents tetrahydrofuran, ether, benzene, toluene etc. are preferred If the acylation is conducted with active esters, as solvents alcohols, such as ethanol or tetrahydrofuran are preferred Acylation is carried out at room temperature or at the boiling point of the reaction mixture.

The reaction mixture is preferably processed by purifying the reaction mixture from the formed side products, such as hydrochloric acid or active alcohol. For this purpose, mild alkaline extraction is used with a suitable solvent. After removing the organic layer the product is obtained optionally after evaporation of the solvent.

In order to prepare an end-product containing pyrrolidine the double bond of the pyrroline ring in the product can be saturated. Reduction is preferably performed by catalytic hydrogenation in the presence of a catalyst. As a catalyst one can use the conventional suitable hydrogenating catalysts, such as palladium, platina, Raney-nickel, etc. One can preferably perform the hydrogenation in the presence of palladium/charcoal (5–10%) catalyst at room temperature, at atmospheric pressure in an alcoholic solution. Hydrogenation is continued until the reaction mixture ceases to consume hydrogen. After evaporation of the solvent the product is suitable for salt formation without further purification.

The active esters are prepared by methods known per se. The characteristics data of the esters are summarized in Table III. The preparation of the esters is disclosed in Examples 6 and 7.

The new phthalimide derivatives and salts of the Formula IC

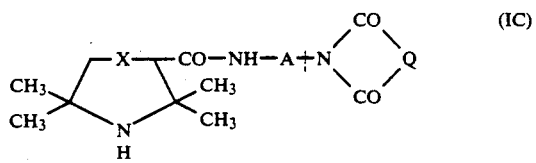

according to the invention can be prepared by a) reacting a carboxamide derivative of the Formula II with the phthalic acid anhydride derivative of the Formula V

preferably in the presence of an aprotic solvent or b) a carboxylic acid of the Formula VIII

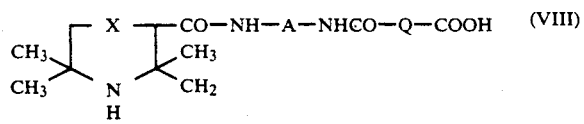

is heated preferably in the presence of an aprotic solvent or c) a carboxamide derivative of the Formula II is reacted with the phthalimide derivative of the Formula VI, preferably without any solvent.

According to variants a) or b) of this process one can preferably proceed by conducting the reaction in the presence of trialkylamine or benzene or toluene at the boiling point of the reaction mixture. The reaction mixture is worked up by distilling the solvent and the optionally used trialkylamine, preferably at reduced pressure. From the residue or the cooled melt acid addition salts can be formed which are purified by crystallization.

In order to prepare a compound of the Formula I containing pyrrolidine, one can use an amine containing pyrrolidine of the Formula II as starting material. One can also prepare a product containing a pyrroline ring and one can saturate the double bond of the pyrroline ring of the phthalimide derivative. The reduction is preferably carried out by catalytic hydrogenation in the presence of platina, palladium, Raney-nickel etc. catalysts. The hydrogenation is preferably performed in the presence of 5–10 per cent palladium/charcoal catalyst at room temperature and at atmospheric pressure until the ceasing of the consumption of the hydrogen gas. As a solvent alcohol is preferred. The product is isolated after evaporation of the solvent. Condensation is performed in an aprotic solvent at the boiling point of the reaction mixture preferably simultaneous removal of water and as aprotic solvent benzene or toluene can be used.

The reaction mixture can preferably be worked up by evaporating the solvent and by dissolving the residue in absolute ethanol, acidifying the mixture of pH=3 by adding ethyl alcohol saturated with hydrochloric acid gas by dissolving the residue in anhydrous acetone and acidifying the mixture by introducing HCl gas.

The product can be crystallized preferably from alcohol-ether and thus a pure product can be obtained.

The compounds of the Formula VII can be prepared by a method known from the article (J. Med. Chem. 10, 1182, 1967) from anthranilic acid and acetic acid anhydride.

The compounds of the Formula II used in the above synthesis are new. They can be prepared by reacting 2,2,6,6-tetramethyl-2,6-dibromo-piperidine-4-one or HBr salt thereof (Ann. Chem. 322, 1902, 77) with a suitable diaminoalkane in aqueous solution and by optional hydrogenation of the product.

The starting oxo compounds of the Formula III (aldehydes and ketones) can be prepared by known methods.

The starting methods of the Formula VIII are new. They can be prepared from carboxamide and phthalic acid anhydride derivative of the Formula V by reacting said compound in the presence of tetrahydrofuran at room temperature.

In order to prepare new quinazolone derivatives of the Formula ID

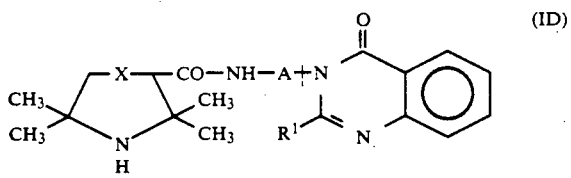

a carboxamide derivative of the Formula II is condensed with a benzoxazinone derivative of the Formula VII and the obtained quinazolinone derivative is reacted with an acid to form a salt, if desired.

The present invention provides also a process for the preparation of the salts of the compounds of the Formula I. Salts can be formed from organic or inorganic acids, such as hydrochloric acid, sulphuric acid, acetic acid, fumaric acid, para-toluene-sulphonic acid or acid ions and from one salt another salt can be prepared or the free base can be set free from the salts.

The compounds of the Formula I or salts thereof according to the present invention can be formulated into pharmaceutical compositions by known methods. As excipients solvents, diluents, carriers, lubricants, adhesives and other additives can be used. The product according to the invention can be combined with other biologically active additives. Further details of the present invention can be found in the following examples.

EXAMPLE 1

1-[N-(2,2,5,5-Tetramethyl-3-pyrroline-3-carbonyl)]-3-[N'-(2-pyrrol-methyl)] propylene-diamine (Table I, No. 45)

6.76 g. N-(3-Amino-propyl)-2,2,5,5-tetramethyl-3-pyrroline-3-carboxamide and 2.85 g. 2-pyrrolcarbaldehyde are dissolved in benzene and the solution is boiled for 8 hours, cooled to room temperature and the crystallized 1-[N-(2,2,5,5-tetramethyl-3-pyrroline-3-carbonyl)]-3-[N'-(2-methylene-pyrrol)]-propylene-diamine is filtered off, washed with hexane and dried.

Yield: 7.9 g. (87 %). Melting point: 115°–117° C. Analysis for the Formula $C_{17}H_{26}N_4O$ (302.43): Calculated: C 67.52, H 8.67, N 18.53 %; Found: C 67.38, H 8.41, N 18.37 %.

NMR-data: $^1$H-NMR (DMSO-$d_6$), =1.14 (s, 6H, 2CH$_3$); 1.26 (s, 6H, 2CH$_3$); 1.45–2.05 (m, 2H, CH$_2$); b 2.70–3.65 (m,4H, 2CH$_2$); 6.00–6.45 (m,3H3 pyrrole CH=); 6.20 (s,1H,pyrroline CH=); 8.05 (s,1H,N=CH) ppm.

7.25 g. of the product are dissolved in 100 ml. ethanol and reduced with 2.5 g. sodium borohydride by boiling the mixture for one hour. The solvent is evaporated and the residue is diluted with 30 ml. water, extracted with chloroform, dried and evaporated. The residual oil is dissolved in ethanol containing hydrochloric acid whereafter the mixture is crystallized with ether. As a product 6.3 g. (69%) dihydrochloride are obtained. The data of the product are contained in Table I.

EXAMPLE 2

1-[N-(2,2,5,5-Tetramethyl-3-pyrroline-3-carbonyl)]-2-hydroxy-3-[N'-(2-thienyl-methyl)]-propylene-diamine (Table I, No. 46)

4.82 g. 1-[N-(2,2,5,5-Tetramethyl-3-pyrroline-3-carbonyl)]-2-hydroxy-3-diamino-propane are admixed with 3.36 g. 2-thiophene carbaldehyde and the mixture is reacted for 4 hours at 110°–110° C. The cooled red oil is suspended with ether. The precipitated 1-[N-(2,2,5,5-tetramethyl-3-pyrroline-4-carbonyl)]-2-hydroxy-3-[N'-(2-methylene-thienyl)]-propylene-diamine is filtered off. Yield: 6.0 g. (89 %). Melting point: 154°–157° C.

Analysis for the Formula $C_{17}H_{25}N_3O_2S$ (335.49): Calculated: C 60.81, H 7.51, N 12.53, S 9.56 %; Found: C 60.59, H 7.38, N 12.35, S 9.43 %.

NMR data: $^1$H-NMR (CDCl$_3$); =1.24 (s,6 H,2CH$_3$); 1.42 (s,6H,2CH$_3$); 3.35–4.25 (m,5H,CH$_2$CHCH$_2$); 6.10 (s,1H, pyrroline CH=); 6.95–7.45 (m, 3H,thienyl CH=); 8.34 (s,1H,N=CH) ppm.

5.8 g. of the product are reduced according to Example 1. From the reduced base (base No. 46), the dihydrochloride of the product is prepared by introducing HCl gas to 150 ml. of a solution of the base in dry acetone to pH=3. the precipitated product is filtered and recrystallized from ethyl alcohol by dilution with ether. Yield: 4.5 g. The data of the product are contained in Table I.

EXAMPLE 3

1-[N-(2,2,5,5-Tetramethyl-3-pyrroline-3-carbonyl)]-3-N'-(2-thienyl-methyl)-propylene-diamine (Table I, No. 50)

a) 4.55 g. of N-(3-aminopropyl)-2,2,5,5-tetramethyl-pyrrolidine-3-carboxamide are dissolved in 150 ml. benzene and to the solution 2.24 g. of 2-thiophene-carbaldehyde are added. The mixture is heated for 6 hours whereafter the solvent is evaporated and the residue is dissolved in 100 ml. of ethanol and reduced with 2 g. sodium borohydride by boiling. After evaporating the solvent the residue is admixed with water. The residual oil is acidified to pH=3 by adding ethanol saturated with HCl gas. The mixture is crystallized with ether. Yield: 4.5 g. (57 %).

b) 2.25 g. of N-(3-amino-propyl)-2,2,5,5-tetramethyl-3-pyrroline-3-carboxamide and 1.2 g. of 2-thiophene carbaldehyde are boiled for 6 hours in 150 ml. benzene solution in a flask equipped with water condenser and cooler whereafter the cooled benzene solution is hydrogenated with 2 g. (5%) palladium/charcoal catalyst at atomspheric pressure until consumption of 2 mole of hydrogen. The solution is filtered, the solvent is evaporated and the residue is dissolved in acetone and acidified to pH=3 by the introduction of HCl gas. The mixture is recrystallized from a mixture of alcohol and ether. The product No. 50 can be recrystallized from a mixture of alcohol and ether. Yield: 2.35 g. (59%).

The melting point and analysis data as well as $^1$N-NMR data of the product obtained by method a) and b) are identical. Similarly were prepared the 75 compounds given in Table I.

EXAMPLE 4

3.03 g. 2-allyl-4-methyl-phenoxyacetic acid succinimide ester (III/7) and 2.11 g. N-(2-amino-ethyl)-2,2,5,5-tetramethyl-3-pyrroline-3-carboxamide are stirred in 50 ml. of an ethanol solution at room temperature. The solvent is distilled off after 4 hours and the residue is dissolved in 15 ml. of water and extracted with chloroform. The combined chloroform solution is dried, filtered and evaporated. The residual oil is acidified to pH=4 by adding ethanol saturated with HCl. The obtained N-(2-allyl-4-methyl-phenoxyacetyl)-N'-2,2,5,5-tetramethyl-3-pyrroline-3-carbonyl)-1,2-ethylene-diamine is filtered and recrystallized from the mixture of ethylalcohol and ether. Yield: 2.6 g. (60 %). The data of the product are contained in Table I (No. 10).

EXAMPLE 5

To a solution of 4.5 g. N-(3-aminopropyl)-2,2,5,5-tetramethyl-3-pyrroline-3-carboxamide in 100 ml. of benzene a solution of 2.5 g. 2-thiophene-carboxylic acid chloride in 20 ml. of benzene are added dropwise at room temperature. The mixture is stirred for 5 hours and the HCl salt of N-(2,2,5,5-tetramethyl-3-pyrroline-3-carbonyl-N'-(2-thiophene-carbonyl)-1,3-propylene-diamine is filtered, washed with ether and dried. The mixture is recrystallized from a little amount of ethyl alcohol. Yield: 2.85 g. (76 %). The data of the product are contained in Table I (No. 15).

EXAMPLE 6

Starting Material 90.14 g. N-(3-amino-propyl)-2,2,5,5-tetramethyl-3-pyrroline-3-carboxamide are dissolved in 300 l. chloroform and hydrogenated at room temperature in the presence of highly active palladium/charcoal catalyst until the ceasing of the hydrogen consumption. The solution is evaporated and the residual viscous oil is directly used for further reactions. Yield: quantitative.

EXAMPLE 7

Equivalent amounts of the reactants according to Example 4 are boiled for 3 hours in chloroform. The solution is cooled, extracted with saturated sodium chloride solution, boiled with water, dried above magnesium sulphate and filtered. The filtrate is evaporated and the residue is acidified to pH=3 by the addition of ethanol saturated with hydrochloric acid. The mixture is crystallized from aqueous ethyl acetate. The product according to Example 4 is obtained. Yield: 70 %. The data of the product are summarized in Table I (compound No. 10).

EXAMPLE 8

2.35 g. pentachlorophenol 2-methoxy-4-allylphenoxyacetate and 2.25 g. N-(3-amino-propyl)-2,2,5,5-tetramethyl-3-carboxamide are boiled for 3 hours in 50 ml. chloroform. The solution is cooled and worked up according to Example 7. N-(2-methoxy-4-allyl)-phenoxy-acetyl-N'-(2,2,5,5-tetramethyl-3-pyrroline-3-carbonyl)-1,3-propylene-diamine is obtained. Yield: 43 %. (Table I. compound No. 9).

EXAMPLE 9

Starting Material

To a solution of 12.8 g. of 2-thiophene carboxylic acid and 11.5 g. N-hydroxy-succinimide in 200 ml. anhydrous ethyl acetate a solution of 1.6 g. dicyclohexylcarbodiimide in 100 ml. ethylacetate is added at 0° C. The reaction mixture is stirred at room temperature for 16 hours, the obtained side product (dicyclohexylurea) is filtered off and the filtrate is evaporated to dryness. The residue is suspended in ether and filtered. The product can be recrystallized from the mixture of chloroform and ether. As a product 20.6 g. of 2-thiophene-carboxylic acid succinic ester are obtained (91 %) (Table III No. 9).

EXAMPLE 10

Starting Material

A suspension of 2.2 g. 2-methoxy-4-allyl-phenoxy acetic acid and 2.6 g. pentachlorophenol in dry ethyl acetate is cooled to 0° C. and a solution of 2 g. dicyclohexylcarbodiimide (DCC) in anhydrous ethyl acetate is added dropwise under stirring. After 3 hours the precipitated dicyclohexyl is filtered off and the filtrate is evaporated to dryness at a pressure of 10–12 Hgmm. and the residue is suspended in ether and filtered. As a product 3.5 g. (85 %) pentachlorophenyl-2-methoxy-4-allyl-phenoxy-acetate are obtained. (Table III, compound No. 16).

EXAMPLE 11

4.22 g. N-(2-aminoethyl)-2,2,5,5-tetramethyl-3-pyrroline-3-carboxamide, 5.1 ml. triethylamine and 2.95 g. phthalic acid anhydride are boiled for 8 hours in 100 ml. of toluene. During this time the amount of water which can be expected in the reaction is collected in the used water condenser trap. The solvent and the excess of triethylamine are distilled off at reduced pressure and the residual oil is dissolved in 30 ml. of ethanol saturated with hydrochloric acid gas and the mixture is treated with active charcoal and crystallized by dilution of a mixture of ethyl acetate and ether. The product is filtered, washed with ether and dried.

As a product N-[2-(2,2,5,5-tetramethyl-3-pyrroline-3-carbonyl)-aminoethyl-phthalimide is obtained. (Table I compound No. 59).

EXAMPLE 12

6.75 g. N-(3-amino-propyl)-2,2,5,5-tetramethyl-3-pyrroline-3-carboxamide and 4.41 g. phthalimide are heated to max. 150° C. After 1–3 hours the ammonia evolution ceases. To the cooled melt 30 ml. of ethanol saturated with hydrochloric acid are added and treated with charcoal and filtered. The filtrate is diluted with ether. Next day the hydrochloric acid salt of N-[3-2,2,5,5-tetramethyl-3-pyrroline-3-carbonyl)-amino-propyl]-phthalimide (Table III, compound No. 60) is filtered off.

EXAMPLE 13

0.373 g. of N-(2,2,5,5-tetramethyl-3-pyrroline-3-carbonyl-N'-(2-carboxy-benzoyl)-1,3-diaminopropane (Table I, compound No. 68), 0.20 g. triethylamine are boiled in 50 ml. of toluene for 10 hours in a flask equipped with water condensing trap. The solvent and the triethylamine are evaporated at reduced pressure. The residue is dissolved in 5 ml. of ethanol containing HCl. and crystallized after dilution with ether. As a product 0.35 g. of N-(3-2,2,5,5-tetramethyl-3-pyrroline-3-carbonyl)-aminopropyl]-phthalimide (Table I, compound No. 58) is obtained. Yield: 90 %.

The physical constants and the spectral data of the product are identical with those of the product obtained from N-(3-aminopropyl-2,2,5,5-tetramethyl-3-pyrroline-3-carboxamide and phthalic acid anhydride or phthalimide.

EXAMPLE 14

Starting material 4.51 g. of N-(3-aminopropyl)-2,2,5,5-tetramethyl-3-pyrroline-3-carboxamide and 2.96 g. of phthalic acid anhydride are dissolved in 200 ml. of tetrahydrofuran and the solution is stirred for 2 hours. The precipitated N-(2,2,5,5-tetramethyl-3-pyrroline-3-carbonyl)-N'-(2-carboxybenzoyl)-1,3-diaminopropane (Table I, compound No. 68) is filtered and crystallized from the mixture of ethyl acetate and chloroform.

The compounds of Table III can be prepared from the appropriate amines by reacting same with cis-4-tetrahydrophthalic acid anhydride or hexahydro phthalic acid anhydride by analogous manner.

EXAMPLE 15

4.83 of 2-methyl-benzoxazinone and 6.76 g. of N-(3-amino-propyl)-2,2,5,5-tetramethyl-3-pyrroline-3-carboxamide are dissolved in 150 ml. toluene and the mixture is boiled under a cooler equipped with a water condensor trap until the expected amount of water is collected in the trap (about 8 hours). The solvent is evaporated in vacuo and the residue is dissolved in 100 ml. of anhydrous acetone and acidified to pH=3 by introducing HCl gas. 2-methyl-3-[3-(2,2,5,5-tetramethyl-3-pyrroline-3-carbonyl-amino)-proyl]-quinazoline-4(3H)-one is obtained in the form of HCl salt (Table I compound No. 70) and the product is filtered, washed with ether and dried. It can be recrystallized from ethanol, diluted with ether.

TABLE I $R^1$—CONH—A—$R^2$

| No | $R^1$ | A | $R^2$ | Yield % | m.p. °C. |
|---|---|---|---|---|---|
| 1. | 2,2,5,5-tetramethyl-3-pyrroline | —CHG$_2$—CH$_2$— | —NH—CO—C$_6$H$_3$(O—)(OEt) (benzodioxole-type) | 35 | 232–233 |
| 2. | 2,2,5,5-tetramethyl-3-pyrroline | —CH$_2$—CH$_2$—CH$_2$— | —NH—CO—C$_6$H$_2$(OCH$_3$)$_3$ | 50 | 196–198 |
| 3. | 2,2,5,5-tetramethyl-3-pyrroline | —CH$_2$—CH$_2$—CH$_2$— | —NH—CO—CH$_2$—C$_6$H$_5$ | 45 | 125–126 |
| 4. | 2,2,5,5-tetramethyl-3-pyrroline | —CH$_2$—CH$_2$—CH$_2$— | —NH—CO—CH$_2$—C$_6$H$_4$—OH | 50 | 79–80 |
| 5. | 2,2,5,5-tetramethyl-3-pyrroline | —CH$_2$—CH$_2$— | —NH—CO—CH(OH)—C$_6$H$_5$ | 63 | 205–206 |
| 6. | 2,2,5,5-tetramethyl-3-pyrroline | —CH$_2$—CH$_2$—CH$_2$— | —NH—CO—CH(OH)—C$_6$H$_5$ | 55 | 145–147 |

TABLE I-continued
R¹—CONH—A—R²
| # | R¹ | A | R² | Yield | mp |
|---|---|---|---|---|---|
| 7. |  | —CH₂—CH₂—CH₂— |  | 68 | 92–99 |
| 8. |  | —CH₂—CH₂—CH₂— |  | 75 | 132–134 |
| 9. |  | —CH₂—CH₂—CH₂— |  | 73 | 158–160 |
| 10. |  | —CH₂—CH₂— |  | 60 | 162–164 |
| 11. |  | —CH₂—CH₂—CH₂— | 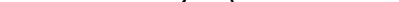 | 55 | 134–136 |
| 12. |  | —CH₂—CH₂—CH₂— |  | 56 | 107–108 |
| 13. |  | —CH₂—CH₂— |  | 70 | 170–173 |
| 14. |  | —CH₂—CH₂— |  | 55 | 110–112 |
| 15. |  | —CH₂—CH₂—CH₂— |  | 76 | 132–135 |
| 16. |  | —CH₂—CH—CH₂—<br>         OH |  | 55 | 208–209 |

TABLE I-continued

R¹—CONH—A—R²

| No. | R¹ | A | R² | Yield | mp |
|---|---|---|---|---|---|
| 17. | 2,2,5,5-tetramethyl-3-methyl-2,5-dihydro-1H-pyrrole (NH) | —CH₂—CH₂—CH₂—CH₂— | —NH—C(O)—(2-thienyl) | 66 | 112–115 |
| 18. | 2,2,5,5-tetramethyl-3-methyl-2,5-dihydropyrrole (N, no H) | —CH₂—CH₂— | —NH—C(O)—CH₂—(2-thienyl) | 61 | 160–163 |
| 19. | 2,2,5,5-tetramethyl-3-methyl-2,5-dihydro-1H-pyrrole (NH) | —CH₂—CH₂—CH₂— | —NH—C(O)—CH₂—(2-thienyl) | 55 | 228–230 |
| 20. | 2,2,5,5-tetramethyl-3-methyl-2,5-dihydro-1H-pyrrole (NH) | —CH₂—CH(OH)—CH₂— | —NH—C(O)—CH₂—(2-thienyl) | 55 | 136–138 |
| 21. | 2,2,5,5-tetramethyl-3-methyl-2,5-dihydro-1H-pyrrole (NH) | —CH₂—CH₂— | —NH—C(O)—CH₂—O—(2-OCH₃, 4-CH₃CH=CH-phenyl) | 60 | 161–163 |
| 22. | 2,2,5,5-tetramethyl-3-methyl-2,5-dihydro-1H-pyrrole (NH) | —CH₂—CH₂—CH₂— | —NH—C(O)—CH(CH₃)—O—(2-OCH₃, 4-CH₃CH=CH-phenyl) | 58 | 170–172 |
| 23. | 2,2,5,5-tetramethyl-3-methyl-2,5-dihydro-1H-pyrrole (NH) | —CH₂—CH₂— | —NH—C(O)—C(CH₃)₂—O—(4-Cl-phenyl) | 69 | 179–181 |
| 24. | 2,2,5,5-tetramethyl-3-methyl-2,5-dihydro-1H-pyrrole (NH) | —CH₂—CH₂—CH₂— | —NH—C(O)—C(CH₃)₂—O—(4-Cl-phenyl) | 74 | 196–198 |
| 25. | 2,2,5,5-tetramethyl-3-methyl-2,5-dihydro-1H-pyrrole (NH) | —CH₂—CH(OH)—CH₂— | —NH—C(O)—C(CH₃)₂—O—(4-Cl-phenyl) | 61 | 211–215 |
| 26. | 2,2,5,5-tetramethyl-3-methyl-2,5-dihydro-1H-pyrrole (NH) | —CH₂—CH₂— | —NH—C(O)—CH₂—O—(2,4-diCl-phenyl) | 39 | 223–226 |

TABLE I-continued
R¹—CONH—A—R²
| # | R¹ | A | R² | Yield | mp |
|---|---|---|---|---|---|
| 27. | 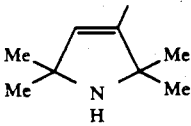 | —CH₂—CH₂—CH₂— | 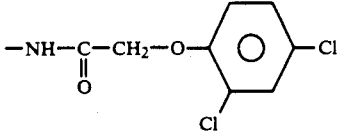 | 62 | 156–157 |
| 28. | 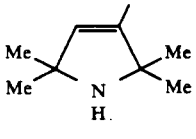 | —CH₂—CH₂— | 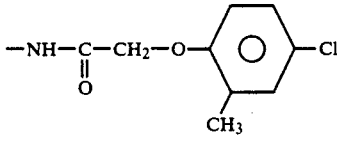 | 46 | 226 (bemlik) |
| 29. | 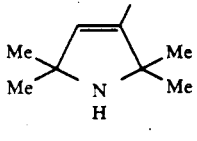 | —CH₂—CH₂—CH₂— | 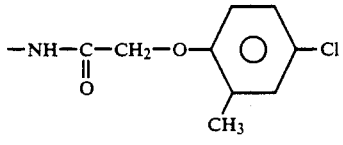 | 50 | 187–188 |
| 30. | 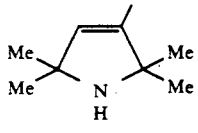 | —CH₂—CH₂— | 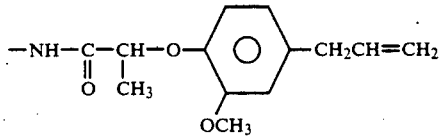 | 62 | 104–106 |
| 31. | 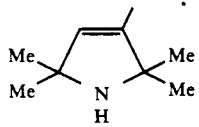 | —CH₂—CH₂—CH₂— | 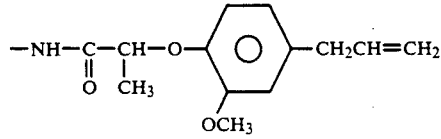 | 60 | 140–147 |
| 32. | 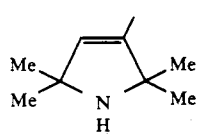 | —CH₂—CH₂— | 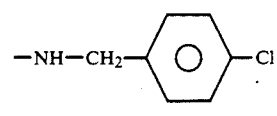 | 80 | 255–257 |
| 33. | 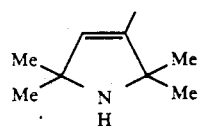 | —CH₂—CH₂— | 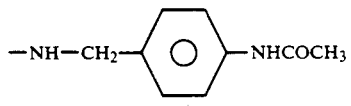 | 54 | 213–124 |
| 34. | 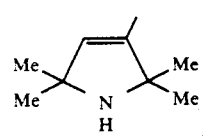 | —CH₂—CH₂— | 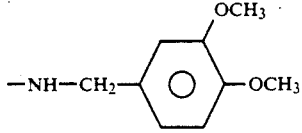 | 60 | 239–241 |
| 35. | 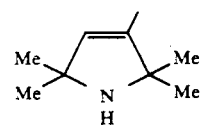 | —CH₂—CH₂— | 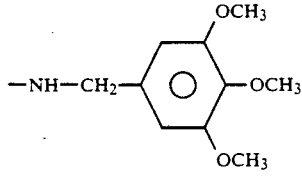 | 68 | 227–228 |
| 36. | 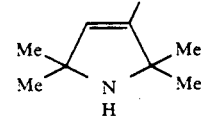 | —CH₂—CH₂— | 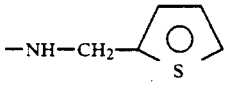 | 70 | 226–229 |

TABLE I-continued
R¹—CONH—A—R²
| # | R¹ | A | R² | Yield | mp |
|---|---|---|---|---|---|
| 37. | 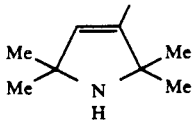 | —CH₂—CH₂— | 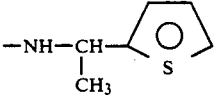 | 68 | 214–216 |
| 38. | 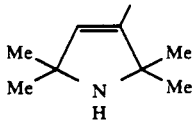 | —CH₂—CH₂—CH₂— | 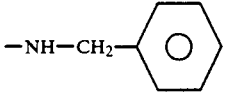 | 73 | 217–221 |
| 39. | 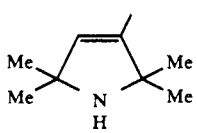 | —CH₂—CH₂—CH₂— | 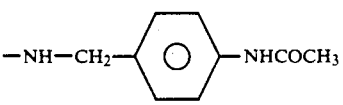 | 65 | 184–185 |
| 40. | 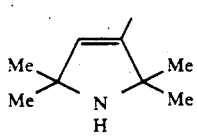 | —CH₂—CH₂—CH₂— | 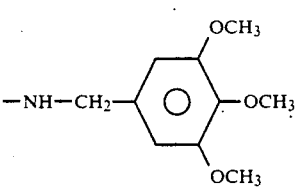 | 73 | 212–213 |
| 41. | 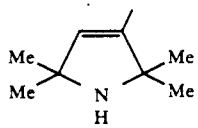 | —CH₂—CH₂—CH₂— | 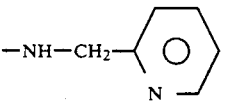 | 70 | 170 higroszkopos |
| 42. | 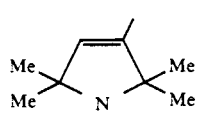 | —CH₂—CH₂—CH₂— | 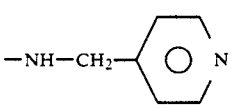 | 41 | 178–180 |
| 43. | 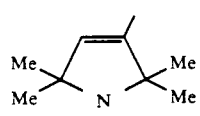 | —CH₂—CH₂—CH₂— | 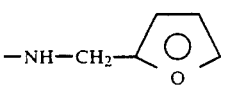 | 62 | 220–222 |
| 44. | 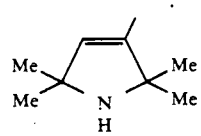 | —CH₂—CH₂—CH₂— | 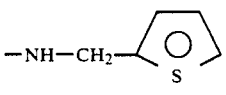 | 65 | 230–231 |
| 45. | 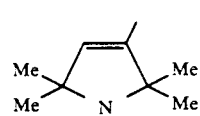 | —CH₂—CH₂—CH₂— | 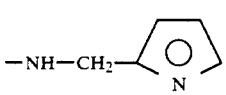 | 69 | 197–198 |
| 46. | 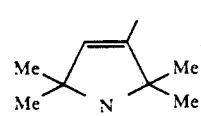 | —CH₂—CH—CH₂—<br>         OH | 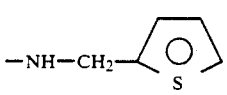 | 64 | 208–211 |
| 47. | 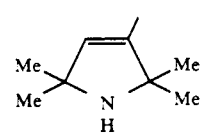 | —CH₂—CH—<br>         CH₃ | 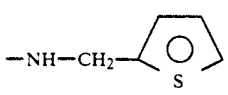 | 63 | higroszkópos |

TABLE I-continued

R¹—CONH—A—R²

| # | R¹ | A | R² | Yield | mp |
|---|---|---|---|---|---|
| 48. | 2,2,5,5-tetramethyl-3-methyl-2,5-dihydro-1H-pyrrole (Me, Me, Me, Me, NH) | –CH₂–C(CH₃)₃ (–CH₂–C(CH₃)(CH₃)CH₃) | –NH–CH₂–(2-thienyl) | 54 | 260 |
| 49. | 2,2,5,5-tetramethyl-3-methyl-2,5-dihydro-1H-pyrrole | –CH₂–CH₂–CH₂–CH₂– | –NH–CH₂–(2-thienyl) | 49 | 250 |
| 50. | 2,2,6,6-tetramethyl-4-methyl-1,2,5,6-tetrahydropyridine | –CH₂–CH₂–CH₂– | –NH–CH₂–(2-thienyl) | 57 | 140–143 |
| 51. | 2,2,6,6-tetramethyl-4-methyl-1,2,5,6-tetrahydropyridine | –CH₂–CH₂–CH₂– | –NH–CH₂–C₆H₄–CF₃ | 61 | 148–150 |
| 52. | 2,2,6,6-tetramethyl-4-methylpiperidine | –CH₂–CH₂–CH₂– | –NH–CH₂–C₆H₄–CF₃ | 76 | 250 |
| 53. | 2,2,6,6-tetramethyl-4-methyl-1,2,5,6-tetrahydropyridine | –CH₂–CH₂–CH₂– | –NH–CH₂–(2-thienyl) | 96 | 230–234 |
| 54. | 2,2,6,6-tetramethyl-4-methylpiperidine | –CH₂–CH₂–CH₂– | –NH–CH₂–(2-thienyl) | 48 | 160–162 |
| 55. | 2,2,5,5-tetramethyl-3-methyl-2,5-dihydro-1H-pyrrole | –CH₂–CH₂– | hexahydrophthalimido | 78 | 176–180 |
| 56. | 2,2,5,5-tetramethyl-3-methyl-2,5-dihydro-1H-pyrrole | –CH₂–CH₂–CH₂– | hexahydrophthalimido | 89 | 180–182 |
| 57. | 2,2,5,5-tetramethyl-3-methyl-2,5-dihydro-1H-pyrrole | –CH₂–CH₂– | 1,2,3,6-tetrahydrophthalimido | 86 | 185–188 |

TABLE I-continued

R¹—CONH—A—R²

| # | R¹ | A | R² | Yield | MP |
|---|----|----|----|-------|-----|
| 58. | 2,2,5,5-tetramethyl-3-methyl-2,5-dihydro-1H-pyrrole (NH) | —CH₂—CH₂—CH₂— | 4-cyclohexene-1,2-dicarboximido (N-) | 88 | 108–110 |
| 59. | 2,2,5,5-tetramethyl-3-methyl-2,5-dihydro-1H-pyrrole (NH) | —CH₂—CH₂— | phthalimido with fused cyclohexene (N-) | 92 | 230 |
| 60. | 2,2,5,5-tetramethyl-3-methyl-2,5-dihydro-1H-pyrrole (NH) | —CH₂—CH₂—CH₂— | phthalimido with fused cyclohexene (N-) | 60 | 250–252[b] |
| 61. | 2,2,5,5-tetramethyl-3-methyl-2,5-dihydro-1H-pyrrole (NH) | —CH₂—CH(OH)—CH₂— | phthalimido with fused cyclohexene (N-) | 70 | 241–242 |
| 62. | 2,2,5,5-tetramethyl-3-methyl-pyrrolidine (NH) | —CH₂—CH₂—CH₂— | phthalimido with fused cyclohexene (N-) | 50 | 124–124 |
| 63. | 2,2,5,5-tetramethyl-3-methyl-2,5-dihydro-1H-pyrrole (NH) | —CH₂—CH₂— | 2-(cyclohexane)carboxy-1-carboxamido | 90 | 135–136 |
| 64. | 2,2,5,5-tetramethyl-3-methyl-2,5-dihydro-1H-pyrrole (NH) | —CH₂—CH₂—CH₂— | 2-(cyclohexane)carboxy-1-carboxamido | 94 | 136–138 |
| 65. | 2,2,5,5-tetramethyl-3-methyl-2,5-dihydro-1H-pyrrole (NH) | —CH₂—CH₂— | 2-(4-cyclohexene)carboxy-1-carboxamido | 93 | 186–188 |
| 66. | 2,2,5,5-tetramethyl-3-methyl-2,5-dihydro-1H-pyrrole (NH) | —CH₂—CH₂—CH₂— | 2-(4-cyclohexene)carboxy-1-carboxamido | 94 | 88–90 |
| 67. | 2,2,5,5-tetramethyl-3-methyl-2,5-dihydro-1H-pyrrole (N) | —CH₂—CH₂— | 2-(benzene)carboxy-1-carboxamido | 86 | 182–184 |

TABLE I-continued

R¹—CONH—A—R²

| No. | R¹ | A | R² | Yield % | m.p. °C |
|---|---|---|---|---|---|
| 68. | 2,2,6,6-tetramethyl-4-methyl-1,2,3,6-tetrahydropyridine (Me,Me,Me,Me,NH) | —CH₂—CH₂—CH₂— | phenyl with COOH and CONH— (ortho) | 93 | 127–128 |
| 69. | (same ring) | —CH₂—CH₂— | benzo-fused with C(=O)N(Me)—C(CH₃)=N— | 70 | 218–220 |
| 70. | (same ring) | —CH₂—CH₂—CH₂— | benzo-fused with C(=O)N(Me)—C(CH₃)=N— | 53 | 193–194 |
| 71. | (same ring) | —CH₂—CH₂— | benzo-fused with C(=O)N(Me)—C(C₂H₅)=N— | 61 | 218–221 |
| 72. | (same ring) | —CH₂—CH₂—CH₂— | benzo-fused with C(=O)N(Me)—C(C₂H₅)=N— | 66 | 213–215 |
| 73. | 2,2,6,6-tetramethyl-4-methyl-piperidine | —CH₂—CH₂—CH₂— | benzo-fused with C(=O)N(Me)—C(CH₃)=N— | 90 | 125–128 |
| 74. | (saturated piperidine) | —CH₂—CH₂—CH₂— | benzo-fused with C(=O)N(Me)—C(C₂H₅)=N— | 50 | 170–175 |
| 75. | (tetrahydropyridine) | —CH₂—CH(OH)—CH₂— | benzo-fused with C(=O)N(Me)—C(CH₃)=N— | 70 | 201–202 |

| No. 1. | (Molecular formula) 7. | Analyses, % calcd/found C | H | N 8. | Cl | ¹H nmr δ (ppm) 9. |
|---|---|---|---|---|---|---|
| 1 | C₁₉H₂₅N₃O₄·HCl (396.89) | 57.64 / 57.77 | 6.62 / 6.74 | 10.61 / 10.65 | 8.95 / 9.09 | 1.50 (s, 6H, 2CH₃); 1.54 (s, 6H, 2CH₃); 3.25–3.40 (m, 4H, 2CH₂); 5.90 (s, 2H, OCH₂O); 6.22 (s, 1H, CH=); 6.60–7.30 (m, 3H, ArCH=) (D₂O) |
| 2. | C₂₂H₃₃N₃O₅·HCl (455.98) | 57.95 / 57.78 | 7.52 / 7.48 | 9.22 / 9.38 | 7.77 / 7.84 | 1.49 (2, 6H, 2CH₃); 1.60 (s, 6H, 2CH₃); 1.50–2.05 (m, 2H, CH₂); 3.00–3.60 (m, 4H, 2CH₂); 3.66 (s, 3H, OCH₃); 3.74 (s, 6H, 2OCH₃); 6.18 (s, 1H, CH=); 6.92 (s, 2H, ArCH=) (D₂O) |
| 3. | C₂₀H₂₉N₃O₂·HCl (379.95) | 63.23 / 62.99 | 7.96 / 7.98 | 11.06 / 10.89 | 9.33 / 9.62 | 1.60 (s, 6H, 2CH₃); 1.70 (s, 6H, 2CH₃); 1.40–2.00 (m, 2H, CH₂); 3.00–3.55 (m, 4H, 2CH₂); 3.56 (s, 2H, COCH₂); 6.30 (s, 1H, CH=); 7.32 (s, 5H, ArCH=) (D₂O) |

TABLE I-continued

| | | | | | | R¹—CONH—A—R² |
|---|---|---|---|---|---|---|
| 4. | $C_{20}H_{29}N_3O_3$·HCl (395.95) | | | 10.61 10.21 | 8.95 9.15 | 1.55 (s, 2CH₃); 1.64 (s, 2CH₃); 1.40-2.05 (m, CH₂) (14H); 2.80-3.40 (m, 4H, 2CH₂); 3.48 (s, 2H, COCH₂); 6.26 (s, 1H, CH=); 6.65-7.25 (m, 4H, ArCH=) (D₂O) |
| 5. | $C_{19}H_{27}N_3O_3$ (345.45) | 66.06 66.01 | 7.88 7.80 | 12.17 12.14 | — | 1.22 (s, 6H, 2CH₃); 1.34 (s, 6H, 2CH₃); 3.05-3.30 (m, 4H, 2CH₂); 4.90 (s, 1H, CH; 6.14 (s, 1H, CH=); 7.20-7.65 (m, 5H, ArCH=) (DMSO-d₆) |
| 6. | $C_{20}H_{29}N_3O_3$·$C_4H_4O_4$ (475.63) | 60.52 60.57 | 6.99 7.01 | 8.84 9.05 | — | 1.24 (s, 6H, 2CH₃); 1.38 (s, 6H, 2CH₃) 1.30-1.95 (m, 2H, CH₂); 3.05-3.55 5.06 (s, 1H, CH); 6.10 (s, 1H, CH=); 7.15-14 7.65 (m, 5H, ArCH=) (DMSO-d₆) |
| 7. | $C_{20}H_{29}N_3O_3$·HCl (395.95) | 60.67 60.71 | 7.64 7.51 | 10.61 10.53 | 8.95 9.02 | 1.52 (s, 6H, 2CH₃); 1.62 (s, 6H, 2CH₃); 1.50-2.05 (m, 2H, CH₂); 3.00-3.55 (m, 4H, 2CH₂); 4.48 (s, 2H, OCH₂); 6.24 (s, 1H, CH=) 6.32-7.50 (m, 5H, ArCH=) (D₂O) |
| 8. | $C_{24}H_{35}N_3O_4$·HCl (466.02) | 61.86 61.75 | 7.79 7.64 | 9.02 9.21 | 7.61 8.08 | 1.52 (s, 2CH₃), 1.62 (s, 2CH₃), 1.58 (d, CH₃), 1.40-1.85 (m, CH₂) (17H); 2.92-3.40 (m, 4H, 2CH₂) 3.60 (s, 3H, OCH₃); 4.25 (s, 2H, OCH₂); 5.70-6.15 (m, 2H, CH=CH) 6.22 (s, 1H, CH=); 6.50-6.82 (m, 3H, ArCH=) (D₂O) |
| 9. | $C_{24}H_{35}N_3O_4$·HCl (466.02) | 6.186 61.62 | 7.79 7.68 | 9.02 9.10 | 7.61 7.78 | 1.55 (s, 6H, 2CH₃); 1.65 (s, 6H, 2CH₃); 1.40-1.82 (m, 2H, CH₂) 2.70-3.95 (m, 6H, 2CH₂, CH₂) 3.54 (s, 3H, OCH₃); 4.30 (s, 2H, OCH₂); 4.62-5.10 (m, 2H, =CH₂) 5.40-6.05 (m, 1H, CH=); 6.25 (s, 1H, CH=); 6.40-6.85 (m, 3H, ArCH=) (D₂O) |
| 10. | $C_{23}H_{33}N_3O_3$·HCl (436.99) | 63.36 63.28 | 7.85 7.67 | 9.64 9.70 | 8.13 8.20 | 1.52 (s, 6H, 2CH₃); 1.60 (s, 6H, 2CH₃); 1.95 (s, 3H, CH₃); 3.05-3.55 (m, 6H, 2CH₂, CH₂); 4.30 (s, 2H, OCH₂); 4.50-5.10 (m, 2H, =CH₂); 5.35-6.10 (m, 1H, CH=) 6.22 (s, 1H, CH=); 6.35-6.93 (m, 3H, ArCH=) (D₂O) |
| 11. | $C_{24}H_{35}N_3O_3$·HCl (450.02) | 64.05 64.15 | 8.05 8.22 | 9.34 9.44 | 7.88 8.01 | 1.54 (s, 2CH₃), 1.64 (s, 2CH₃), 1.40-1.85 (m, CH₂) (14H); 1.95 (s, 3H, CH₃); 2.60-4.55 (m, 10, 2CH₂, OCH₂, CH₂, =CH₂); 5.50-6.00 (m, 1H, CH=); 6.28 (s, 1H, CH=); 6.40-7.05 (m, 3H, ArCH=) (D₂O) |
| 12. | $C_{20}H_{29}N_3O_2S$·HCl (397.96) | 58.31 58.32 | 7.34 7.41 | 10.20 10.25 | 8.60 8.81 | 7.78 8.02 | 1.62 (s, 6H, 2CH₃); 1.68 (s, 6H, 2CH₃) 1.22-2.04 (m, 2H, CH₂); 2.80-3.54 (m, 4H, 2CH₂); 3.62 (s, 2H, SCH₂); 6.30 (s, 1H, CH=); 7.25-7.34 (m, 5H, ArCH=) (D₂O) |
| 13. | $C_{17}H_{24}N_4O_2$·2HCl (389.34) | 52.45 52.64 | 6.73 6.88 | 14.39 14.55 | 18.21 18.36 | — | 1.52 (s, 6H, 2CH₃); 1.58 (s, 6H, 2CH₃) 3.14-3.55 (m, 4H, 2CH₂); 6.28 (s, 1H, CH=) 8.10-8.22 (m, 2H, 2CH=); 8.80-9.05 (m, 2H, 2CH=) (D₂O) |
| 14. | $C_{16}H_{23}N_3O_2S$·HCl (357.90) | 53.69 53.44 | 6.76 6.57 | 11.74 11.55 | 9.91 9.87 | 8.96 8.76 | 1.52 (s, 6H, 2CH₃); 1.54 (s, 6H, 2CH₃); 3.40-3.50 (m, 4H, 2CH₂); 6.22 (s, 1H, CH=) 7.05-7.70 (m, 3H, 3CH=) (D₂O) |
| 15. | $C_{17}H_{25}N_3O_2S$·HCl (371.93) | 54.90 54.86 | 7.05 7.26 | 11.30 11.45 | 9.53 9.63 | 8.62 8.42 | 1.35 (s, 6H, 2CH₃); 1.45 (s, 6H, 2CH₃) 1.50-1.85 (m, 2H, CH₂); 2.70-3.55 (m, 4H, 2CH₂); 6.38 (s, 1H, CH=); 7.05-7.90 (m, 3H, 3CH=) (DMSO-d₆) |
| 16. | $C_{17}H_{25}N_3O_3S$ (251.49) | 58.10 58.26 | 7.16 7.45 | 11.96 11.70 | — | 9.12 9.08 | 1.20 (s, 6H, 2CH₃); 1.34 (s, 6H, 2CH₃) 2.80-3.80 (m, 5H, CH₂CHCH₂); 6.24 (s, 1H, CH=); 7.80-8.02 (m, 3H, 3CH=) (DMSO-d₆) |
| 17. | $C_{18}H_{27}N_3O_2S$·HCl (385.96) | 56.02 56.22 | 7.31 7.43 | 01.89 10.97 | 9.19 9.24 | 8.31 8.45 | 1.46 (s, 6H, 2CH₃); 1.54 (s, 6H, 2CH₃) 1.22-2.04 (m, 2H, CH₂); 2.40-3.55 (m, 6H, 3CH₂) 6.45 (s, 1H, CH=); 6.80-7.95 (m, 3H, 3CH=) (DMSO-d₆) |
| 18. | $C_{17}H_{25}N_3O_2S$·HCl (371.93) | 54.90 54.93 | 7.05 6.95 | 11.30 11.44 | 9.53 9.50 | 8.62 8.70 | 1.52 (s, 6H, 2CH₃); 1.60 (s, 6H, 2CH₃) 3.25-3.35 (m, 4H, 2CH₂); 3.70 (s, 2H, CH₂); 6.04 (s, 1H, CH=); 6.40-6.85 (m, 3H, 3CH=) (D₂O) |
| 19. | $C_{18}H_{27}N_3O_2S$·HCl (385.96) | 56.02 56.29 | 7.31 7.23 | 10.89 10.76 | 9.19 9.25 | 8.31 8.47 | 1.40 (s, 6H, 2CH₃); 1.50 (s, 6H, 2CH₃) 1.50-1.75 (m, 2H, CH₂); 3.02-3.44 (m, 4H, 2CH₂); 3.76 (s, 2H, CH₂); 6.30 (s, 1H, CH=); 6.90-7.90 (m, 3H, 3CH=) (D₂O) |

TABLE I-continued

R¹—CONH—A—R²

| # | Formula (MW) | C | H | N | Other | NMR |
|---|---|---|---|---|---|---|
| 20. | C-18-H-27-N₃O₃S. (365.46) | 59.16 / 56.89 | 7.44 / 7.32 | 11.50 / 11.57 | — | 8.77 / 9.02 | 1.54 (s, 6H, 2CH₃); 1.64 (s, 6H, 2CH₃) 2.55–3.55 (m, 4H, 2CH₂); 3.60–3.95 (m, CH) 3.78 (s, CH₂), (3H); 6.32 (s, 1H, CH=) 6.85–7.40 (m, 3H, 3CH=) (D₂O) |
| 21. | C₂₃H₃N₃O₄·HCl (452.02) | 61.12 / 60.91 | 7.58 / 7.62 | 9.30 / 9.29 | 7.84 / 7.96 | 1.50 (s, 2CH₃); 1.58 (s, 2CH₃), 1.88 (d, CH₃), (15H); 3.25–3.48 (m, 4H, 2CH₂) 3.70 (s, 3H, OCH₃); 4.34 (s, 2H, OCH₂) 5.85–6.25 (m, 3H, CH=CH, CH=); 6.66–6.85 (m, 3H, ArCH=) (D₂O) |
| 22. | C₂₅H₃₇N₃O₄·HCl (480.05) | 62.55 / 62.63 | 7.98 / 7.82 | 8.75 / 9.02 | 7.38 / 7.52 | 1.40 (d, CH₃), 1.52 (s, 2CH₃), 1.62 (s, 2CH₃), 1.80 (s, CH₃); 1.30–1.90 (m, CH₂) (20H); 2.85–3.30 (m, 4H, 2CH₂); 3.78 (s, 3H, OCH₃); 4.42–4.38 (m, 1H, CH) 6.15–6.45 (m, 3H, CH=CH, CH=); 6.75–7.05 (m, 3H, ArCH=) (DMSO-d₆) |
| 23. | C₂₁H₃₀ClN₃O₃·HCl (444.41) | 56.75 / 56.86 | 7.03 / 6.92 | 9.46 / 9.58 | 15.96 / 15.75 | 1.38 (s, 6H, 2CH₃) 1.52 (s, 6H, 2CH₃) 1.60 (s, 6H, 2CH₃); 3.25–3.55 (m, 4H, 2CH₂); 6.10 (s, 1H, CH=) 6.60–7.30 (m, 4H, ArCH=) (D₂O) |
| 24. | C₂₂H₃₂ClN₃O₃·HCl (458.43) | 57.64 / 57.61 | 7.26 / 7.14 | 9.17 / 9.36 | 15.47 / 15.65 | 1.38 (s, 6H, 2CH₃); 1.58 (s, 6H, 2CH₃) 1.66 (s, 6H, 2CH₃); 1.30–1.95 (m, 2H, CH₂) 2.95–3.55 (s, 4H, 2CH₂); 6.30 (s, 1H, CH=) 6.65–7.30 (m, 4H, ArCH=) (D₂O) |
| 25. | C₂₂H₃₂ClN₃O₄·HCl (474.43) | 55.70 / 65.85 | 7.01 / 7.08 | 8.86 / 8.96 | 14.95 / 15.00 | 1.36 (s, 6H, 2CH₃); 1.54 (s, 6H, 2CH₃); 1.60 (s, 6H, 2CH₃); 3.06–4.05 (m, 5H, CH₂CHCH₂) 6.32 (s, 1H, CH=); 6.70–48 (m, 4H, ArCH=) (D₂O) |
| 26. | C₁₉H₂₅Cl₂N₃O₃·HCl (450.80) | 50.62 / 50.46 | 5.82 / 5.58 | 9.32 / 9.35 | 23.59 / 23.58 | 1.52 (s, 5H, 2CH₃) 1.58 (m, 6H, 2CH₃) 3.25–3.55 (m, 4H, 2CH₂); 4.44 (s, 2H, CH₂O); 6.18 (s, 1H, CH=) 5.65–7.30 (s, 3H, ArCH=) (D₂O) |
| 27. | C₂₀H₂₇Cl₂N₃O₃·HCl (484.82) | 51.68 / 51.90 | 6.07 / 5.92 | 9.04 / 8.91 | 22.28 / 22.34 | 1.54 (s, 6H, 2CH₃); 1.64 (s, 6H, 2CH₃); 1.35–1.85 (m, 2H, CH₂); 2.90–3.60 (m, 4H, 2CH₂); 4.62 (s, 2H, CH₂O); 6.48 (s, 1H, CH=) 6.95–7.60 (m, 3H, ArCH=) |
| 28. | C₂₀H₂₈ClN₃O₃·HCl (430.38) | 55.82 / 55.73 | 6.79 / 6.91 | 9.76 / 9.87 | 16.48 / 16.37 | 1.48 (s, 6H, 2CH₃); 1.54 (s, 6H, 2CH₃); 2.00 (s, 3H, CH₃); 3.20–3.55 (m, 4H, 2CH₂); 4.25 (s, 2H, CH₂O); 6.15 (s, 1H, CH=); 6.35–7.00 (s, 3H, ArCH=) (D₂O) |
| 29. | C₂₁H₃₀ClN₃O₃·HCl (444.41) | 56.76 / 58.94 | 7.03 / 6.96 | 9.45 / 9.37 | 15.96 / 15.72 | 1.52 (s, 6H, 2CH₃); 1.62 (s, 6H, 2CH₃); 1.35–1.80 (m, 2H, CH₂) 2.03 (s, 3H, CH₃) 2.90–3.45 (s, 4H, 2CH₂) 4.25 (s, 2H, CH₂O); 6.24 (t, 1H, CH=); 6.35–7.05 (m, 3H, ArCH=) (D₂O) |
| 30. | C₂₄H₃₅N₃O₄·HCl (466.05) | 61.86 / 61.73 | 7.78 / 7.82 | 9.02 / 9.11 | 7.61 / 7.85 | 1.25–1.65 (s, 15H, 5CH₃); 3.00–3.45 (m, 6H, 2CH₂, =CH₂); 3.72 (t, 3H, OCH₃); 4.60–5.15 (m, 4H, CH₂CH=, CH) 6.08 (s, 1H, CH=); 6.50–6.85 (m, 3H, ArCH=), (D₂O) |
| 31. | C₂₅H₃₇N₃O₄·HCl (480.05) | 62.55 / 62.35 | 7.98 / 7.72 | 6.75 / 6.74 | 7.38 / 7.49 | 1.25–1.85 (m, 17H, 5CH₃, CH₂); 2.80–3.45 (m, 6H, 2CH₂, =CH₂); 3.65 (s, 3H, OCH₃); 4.30–6.10 (s, 4H, CH₂CH=, CH); 6.24 (s, 1H, CH=); 6.35–6.80 (m, 3H, ArCH=) (D₂O) |
| 32. | C₁₈H₂₆ClN₃O 2C₇H₆O₃S (680.28) | 58.53 / 56.67 | 6.22 / 6.12 | 6.18 / 6.36 | 5.21 / 5.36 | 1.45 (s), 1.56 (s), (12H, 4CH₃); 2.70–3.60 (m, 4H, 2CH₂); 4.25 (s, 2H, NCH₂); 6.50 (s, 1H, CH=); 7.04–7.80 (m, 12H, ArCH=) (DMSO-d₆) |
| 33. | C₂₀H₃₀N₄O₂·2HCl (431.43) | 55.68 / 55.57 | 7.48 / 7.38 | 12.99 / 12.74 | 16.44 / 16.70 | 1.50 (s, 6H, 2CH₃); 1.58 (s, 6H, 2CH₃); 2.05 (s, 3H, OCH₃); 3.04–3.75 (m, 4H, 2CH₂); 4.16 (s, 2H, NCH₂); 6.34 (s, 1H, CH=); 7.40 (t, 4H, ArCH=) (D₂O) |
| 34. | C₂₀H₃₁N₃O₃·2C₇H₈C₃S (705.88) | 57.85 / 57.92 | 6.71 / 6.63 | 5.95 / 6.01 | — | 9.09 / 9.25 | 1.35 (s), 1.45 (s) (12H, 4CH₃); 2.10 (t, 6H, 2CH₃); 2.90–3.60 (m, 4H 2CH₂); 3.60 (t, 6H, 2OCH₃); 3.92 (s, 2H, NCH₂); 6.25 (s, 1H, CH=); 6.70–7.60 (s, 11H, ArCH=) (D₂O) |
| 35. | C₂₁H₃₃N₃O₄·2C₇H₈C₃S (735.92) | 57.12 / 57.20 | 6.71 / 7.04 | 5.71 / 5.47 | — | 8.71 / 8.55 | 1.45 (t), 1.54 (s) (12H, 4CH₃); 2.15 (s, 6H, 2CH₃); 2.90–3.60 (m, 4H, 2CH₂); 3.60 (s, 3H, OCH₃); 3.68 (s, 6H, 2OCH₃); 1.96 (s, 2H, NCH₂); 6.25 (s, 1H, CH=); 6.60–7.60 (m, 10H, ArCH=) (D₂O) |
| 36. | C₁₆H₂₅N₃OS 2C₇H₈O₃S | 55.28 / 55.39 | 6.34 / 6.29 | 6.45 / 6.41 | — | 14.76 / 14.88 | 1.50 (s), 1.63 (s) (12H, 4CH₃); 2.30 (s, 6H, 2CH₃); 2.60–3.70 (m, 4H, |

TABLE I-continued $R^1-CONH-A-R^2$

| # | Formula | | | | | | NMR |
|---|---|---|---|---|---|---|---|
| | | | | | | | 2CH$_2$); 4.38 (t, 2H, NCH$_2$); 6.42 (s, 1H, CH=); 7.00–7.70 (m, 11H, ArCH=) (DMSO-d$_6$) |
| 37. | C$_{17}$H$_{27}$N$_3$OS. 2HCl (594.43) | 51.77 51.69 | 7.41 7.60 | 10.65 10.54 | 17.98 18.03 | 8.13 8.24 | 1.62 (s, 6H, 2CH$_3$); 1.68 (s, 6H, 2CH$_3$) 1.79 (d, 3H, CH$_3$); 2.95-3.75 (s, 4H, 2CH$_2$); 4.45-5.05 (m, 1H, CH); 6.42 (t, 1H, CH=) 6.95-7.65 (m, 3H, ArCH=) (D$_2$O) |
| 38. | C$_{19}$H$_{29}$N$_3$C. 2HCl (388.40) | 58.76 56.58 | 8.05 8.17 | 10.82 11.02 | 18.26 18.10 | — | 1.54 (s, 6H, 2CH$_3$); 1.60 (t, 6H, 2CH$_3$); 1.25-1.75 (m, 2H, CH$_2$); 2.85-3.55 (m, 4H, 2CH$_2$), 4.80 (s, 2H, NCH$_2$); 6.24 (s, 1H, CH=); 7.42 (s, 5H, ArCH=) (D$_2$O) |
| 39. | C$_{21}$H$_{32}$N$_4$O$_2$ 2HCl (445.44) | 56.62 56.76 | 7.69 7.60 | 12.58 12.41 | 15.92 16.08 | — | 1.55 (s, 6H, 2CH$_3$); 1.60 (s, 6H, 2CH$_3$) 1.45-2.20 (m, 2H, CH$_2$); 2.16 (s, 3H, OCH$_3$); 2.80-3.55 (m, 4H, 2CH$_2$); 4.20 (s, 2H, NCH$_2$); 6.26 (s, 1H, CH=); 7.44 (s, 4H, ArCH=) (D$_2$O) |
| 40. | C$_{22}$H$_{35}$N$_3$O$_4$ 2HCl (478.45) | 65.23 65.43 | 7.79 7.86 | 8.78 8.90 | 14.82 14.98 | — | 1.50 (s, 12H, 4CH$_3$); 1.60-2.10 (m, 2H, CH$_2$); 2.50-3.50 (m, 4H, 2CH$_2$); 3.70 (s, 3H, OCH$_3$); 3.78 (s, 6H, 2OCH$_3$); 4.71 (s, 2H, NCH$_2$); 6.20 (s, 1H, CH=); 6.20 (s, 2H,.ArCH=) (D$_2$O) |
| 41. | C$_{18}$H$_{28}$N$_4$O 3HCl (425.83) | 51.77 50.64 | 7.34 7.56 | 13.16 13.06 | 24.98 24.79 | — | 1.62 (s, 6H, 2CH$_3$); 1.70 (s, 6H, 2CH$_3$); 18.0-2.30 (m, 2H, CH$_2$); 3.10-3.70 (m, 4H, 2CH$_2$); 4.20 (s, 2H, NCH$_2$); 6.28 (s, 1H, CH=); 7.80-9.05 (m, 4H, 4CH=); (D$_2$O) |
| 42. | C$_{18}$H$_{26}$N$_4$O.H$_2$O 2C$_7$H$_8$O$_3$S (678.82) | 56.62 56.85 | 6.83 6.58 | 8.25 8.46 | — | 9.45 9.33 | 1.55 (s, 6H, 2CH$_3$); 1.60 (s, 6H, 2CH$_3$); 1.50-2.10 (m, 2H, CH$_2$); 2.30 (s, 6H, 2CH$_3$); 2.80-3.50 (m, 4H, 2CH$_2$); 4.20 (s, 2H, NCH$_2$); 6.22 (s, 1H, CH=); 7.00-8.80 (m, 12H, ArCH=) (D$_2$O) |
| 43. | C$_{17}$H$_{27}$N$_3$O$_2$. 2HCl (378.34) | 53.97 54.04 | 7.73 7.60 | 11.11 10.97 | 18.79 18.35 | — | 1.60 (s, 6H, 2CH$_3$); 1.68 (s, 6H, 2CH$_3$); 1.65-2.30 (m, 2H, CH$_2$); 2.90-3.60 (m, 4H, 2CH$_2$); 4.30 (s, 2H, NCH$_2$); 6.34 (s, 1H, CH=); 6.40-7.70 (m, 3H, 3CH=) (D$_2$O) |
| 44. | C$_{17}$H$_{27}$N$_3$OS. 2HCl (394.41) | 51.77 51.88 | 7.41 7.36 | 10.66 10.99 | 17.98 17.77 | 8.13 8.30 | 1.60 (s, 6H, 2CH$_3$); 1.66 (s, 6H, 2CH$_3$); 1.70-2.30 (m, 2H, CH$_2$); 2.80-3.80 (m, 4H, 2CH$_2$); 4.46 (s, 2H, NCH$_2$); 6.30 (s, 1H, CH=); 6.90-7.70 (m, 3H, 3CH=) (D$_2$O) |
| 45. | C$_{17}$H$_{28}$N$_4$O. 2HCl (377.37) | 54.11 52.96 | 8.01 7.97 | 14.85 15.05 | 18.79 19.16 | — | 1.55 (s, 6H, 2CH$_3$); 1.64 (s, 6H, 2CH$_3$); 1.40-2.25 (m, 2H, CH$_2$); 2.55-3.45 (m, 4H, 2CH$_2$); 4.10 (s, 2H, NCH$_2$); 5.95-6.34 m, 2H, 2CH=, pirrol); 5.80-6.90 (m. 1H, CH=, pirrol); 6.52 (s, 1H, CH=, pirrolin) (DMSO-d$_6$) |
| 46. | C$_{17}$H$_{27}$N$_3$O$_2$S. 2HCl (410.41) | 49.76 49.78 | 7.12 7.00 | 10.24 10.49 | 17.28 17.11 | 7.81 7.95 | 1.62 (s, 6H, 2CH$_3$); 1.68 (s, 6H, 2CH$_3$); 2.65-3.55 (m, 4H, 2CH$_2$); 3.75-4.35 (m, 1H, CH); 4.54 (s, 2H, NCH$_2$); 6.36 (s, 1H, CH=); 6.95-7.75 (m, 3H, CH=) (D$_2$O) |
| 47. | C$_{17}$H$_{27}$N$_3$OS. 2HCl (194.43) | 51.77 51.33 | 7.41 7.96 | 10.65 10.88 | 17.98 17.84 | 8.13 8.02 | 1.25-1.45 (m, 3H, CH$_3$); 1.62 (m, 6H, 2CH$_3$ 1.70 (s, 6H, 2CH$_3$); 3.05-3.80 (s, 3H, CH$_2$CH); 4.55 (s, 2H, NCH$_2$); 6.46 (s, 1H, CH=); 6.95-7.75 (m, 3H, 3CH=) (D$_2$O) |
| 48. | C$_{18}$H$_{29}$N$_3$OS. 2HCl (408.44) | 52.93 52.91 | 7.65 7.45 | 10.29 10.44 | 17.36 17.18 | 7.85 8.04 | 1.42 (s, 6H, 2CH$_3$); 1.60 (s, 6H, 2CH$_3$); 1.70 (s, 6H, 2CH$_3$); 3.56 (s, 2H, CH$_2$); 4.50 (s, 2H, CH$_2$); 6.50 (s, 1H, CH=); 6.95-7.55 (m, 3H, CH=) (D$_2$O) |
| 49. | C$_{18}$H$_{29}$N$_3$OS. 2HCl (408.44) | 52.93 52.76 | 7.65 7.80 | 10.29 10.24 | 17.36 17.65 | 7.85 7.97 | 1.62 (s, 2CH$_2$), 1.70 (s, 2CH$_3$), 1.43-1.80 (m, 2CH$_2$); (16H); 2.90-3.80 (s, 4H, 2CH$_2$); 4.45 (s, 2H, NCH$_2$); 6.34 (s, 1H, CH=); 7.00-7.80 (m, 3H, 3CH=) (D$_2$O) |
| 50. | C$_{17}$H$_{29}$N$_3$OS 2HCl (396.44) | 51.51 51.67 | 7.88 7.99 | 10.60 10.49 | 17.89 17.98 | 8.09 8.15 7.04-7.70 (m, 3H, 3CH=) (DMSO-d$_6$) | 1.30-1.74 (m, 12H, 4CH$_3$); 1.75-3.65 (m, 9H, 3CH$_2$, CH$_2$CH); 4.40 (s, 2H, 5CH$_2$) |
| 51. | C$_{20}$H$_{28}$F$_3$H$_3$O. 2HCl (456.39) | 52.63 52.59 | 6.63 6.47 | 9.21 9.24 | 15.54 15.43 | — | 1.56 (s, 6H.2CH$_3$); 1.60 (s, 6H, 2CH$_3$) 1.70-2.20 (s, 2H, CH$_2$); 2.85-3.46 (s, 4H, 2CH$_2$); 4.30 (s, 2H, CH$_2$); 6.30 (s, 1H, CH=); 7.55-7.85 (m, 4H, ArCH=) (C$_2$O) |
| 52. | C$_{20}$H$_{30}$F$_3$N$_3$O. 2HCl (456.41) | 52.40 52.39 | 7.04 6.96 | 9.17 9.26 | 15.47 15.55 | — | 1.05-1.50 (m, 12H, 4CH$_3$); 1.65-2.25 (s, 4H, CH$_2$CH$_2$); 2.55-3.36 (m, 5H. CH 2CH$_2$); 4.16 (s, 2H, CH$_2$); 7.35-7.90 (m, 4H, ArCH=) (D$_2$O) |
| 53. | C$_{17}$H$_{27}$N$_3$OS. 2HCl | 51.77 51.65 | 7.41 7.26 | 10.65 10.58 | 17.98 18.06 | 8.13 8.24 | 1.62 (s, 6H, 2CH$_3$); 1.68 (s, 6H, 2CH$_3$ 1.74-2.25 (s, 2H, CH$_2$); 2.90-3.80 |

TABLE I-continued $R^1-CONH-A-R^2$

| # | Formula (MW) | C | H | N | Other | Other2 | NMR |
|---|---|---|---|---|---|---|---|
| | (394.41) | | | | | | (n, 4H, 2CH$_2$): 4.28 (s, 2H, CH$_2$): 6.30 (s, 1H, CH=): 7.10–7.80 (m, 3H, 3CH=) (D$_2$O) |
| 54. | C$_{17}$H$_{29}$N$_3$OS. 2HCl (396.43) | 51.55 / 51.34 | 7.88 / 7.68 | 10.60 / 10.53 | 17.89 / 17.64 | 8.08 / 8.28 | 1.20–1.65 (m, 12H, 4CH$_3$): 1.70–2.10 (m, 2H, CH$_2$): 2.10–2.40 9m, 2H, CH$_2$) 2.85–3.85 (m, 5H, 2CH$_2$, CH): 4.24 (s, 2H, CH$_2$): 7.10–7.65 (m, 3H, 3CH=) (D$_2$O) |
| 55. | C$_{19}$H$_{29}$N$_3$O$_3$.HCl (381.94) | 59.44 / 59.48 | 7.88 / 7.91 | 10.94 / 10.75 | 9.23 / 9.26 | | [1.56 (s), 1.62 (s), 1.1–1.9 (m)] (20 H, 4CH$_3$, 4CH$_2$): 2.73–3.15 (m, 2H, CH=CH): 3.20–3.85 (m, 4H, CH$_2$CH$_2$): 6.22 (s, 1H, CH=) (D$_2$O) |
| 56. | C$_{20}$H$_{31}$N$_3$O$_3$.HCl (397.95) | 60.37 / 60.41 | 8.11 / 8.30 | 10.56 / 10.65 | 8.91 / 8.85 | | [1.60 (e), 1.68 (s), 1.1–2.0 (m)] (22H, 4CH$_3$, 2CH$_2$, CH$_2$): 2.82–3.75 (m, 6H, 2CH$_2$, CHCH): 6.32 (s, 1H, CH=), (D$_2$O) |
| 57. | C$_{19}$H$_{27}$N$_3$O$_3$.HCl (381.92) | 59.76 / 59.66 | 7.39 / 7.36 | 11.00 / 11.16 | 9.28 / 9.37 | | 1.56 (s, 6H, 2CH$_3$): 1.62 (s, 6H, 2CH$_3$): 2.10–2.45 (m, 4H, CH$_2$CH$_2$): 3.04–3.80 (m, 6H, CH$_2$CH$_2$, CHCH): 5.58–5.99 (m, 2H, CH=CH): 6.20 (s, 1H, CH=) (D$_2$O) |
| 58. | C$_{20}$H$_{29}$N$_3$O$_3$.HCl (395.93) | 60.67 / 60.64 | 7.64 / 7.56 | 10.61 / 10.66 | 8.95 / 8.88 | | [1.55 (s), 1.63 (s), 1.2–2.0 (m)] (14H, 4CH$_3$CH$_2$): 2.04–2.50 (m, 4H, 2CH$_2$): 2.90–3.64 (m, 6H, CH$_2$CH$_2$, CHCH): 5.70–5.90 (m, 2H, CH=CH): 6.30 (s, 1H, CH=) (D$_2$O) |
| 59. | C$_{19}$H$_{23}$N$_3$O$_3$.HCl (377.89) | 60.40 / 60.36 | 6.40 / 6.44 | 11.12 / 11.38 | 9.38 / 9.33 | | 1.40 (s, 6H, 2CH$_3$); 1.52 (s, 6H, 2CH$_3$): 3.30–3.82 (m, 4H, 2CH$_2$): 6.14 (s, 1H, CH=): 7.66 (s, 4H, ArCH=) (D$_2$O) |
| 60. | C$_{20}$H$_{25}$N$_3$O$_3$.HCl (391.90) | 61.30 / 61.47 | 6.69 / 6.88 | 10.72 / 10.55 | 9.05 / 9.38 | | 1.52 (s, 6H, 2CH$_3$): 1.58 (s, 6H, 2CH$_3$): 1.50–2.05 (m, 2H, CH$_2$): 3.02–3.72 (m, 4H, 2CH$_2$): 6.18 (s, 1H, CH=): 7.60 (s, 4H, ArCH=) (D$_2$O) |
| 61. | C$_{20}$H$_{25}$N$_3$O$_4$.HCl (407.92) | 58.89 / 59.03 | 6.42 / 6.32 | 10.30 / 10.25 | 8.69 / 8.89 | | 1.62 (s, 6H, 2CH$_3$): 1.70 (s, 6H, 2CH$_3$): 3.25–3.55 (m, 2H, CH$_2$): 3.55–3.80 (m, 2H, CH$_2$): 3.80–4.35 (m, 1H, CH): 6.34 (s, 1H, CH=): 7.70 (s, 4H, ArCH=) (D$_2$O) |
| 62. | C$_{20}$H$_{27}$N$_3$O$_3$.HCl (393.94) | 60.98 / 60.79 | 7.16 / 7.04 | 10.67 / 10.58 | 9.00 / 8.89 | | 1.10–2.05 (m, 14H, 4CH$_3$, CH$_2$): 2.10–2.45 (d, 2H, CH$_2$): 2.85–3.65 (m, 5H, 2CH$_2$, CH): 7.40–7.65 (m, 4H, ArCH=) (D$_2$O) |
| 63. | C$_{19}$H$_{31}$N$_3$O$_4$ (365.49) | 62.44 / 62.28 | 8.55 / 8.48 | 11.50 / 11.67 | | | [1.59 (s), 1.68 (s), 1.40–2.00 (m)] (22H,4CH$_3$,4CH$_2$,CH$_2$); 2.30–2.84 (m,2H, CHCH); 3.15–3.45 (m,4H,CH$_2$CH$_2$); 6.32 (s,1H,CH=) (D$_2$O) |
| 64. | C$_{20}$H$_{33}$N$_3$O$_4$ (379.52) | 63.30 / 63.17 | 8.76 / 8.60 | 11.07 / 11.02 | | | [1.62 (s), 1.62 (s), 1.20–2.10 (m)] (22H,4CH$_3$,4CH$_2$,CH$_2$); 2.20–2.74 (m, 2H,CHCH); 3.00–3.60 (m,4H,2CH$_2$); 6.30 (s,1H,CH=) (D$_2$O) |
| 65. | C$_{19}$H$_{29}$N$_3$O$_4$ (363.48) | 62.79 / 62.86 | 8.04 / 8.31 | 11.56 / 11.47 | | | 1.59 (s,6H,2CH$_3$); 1.68 (s,6H,2CH$_3$); 2.02–2.42 (m,4H,2CH$_2$); 2.45–3.15 (m, 2H,CHCH); 3.20–3.48 (m,4H,CH$_2$CH$_2$); 5.58–5.78 (m,2H,CH=CH); 6.34 (s,1H, CH=) (D$_2$O) |
| 66. | C$_{20}$H$_{31}$N$_3$O$_4$ (377.51) | 63.64 / 63.50 | 8.28 / 8.40 | 11.13 / 11.02 | | | [1.52 (s,) 1.62 (s), 1.45–2.00 (m,)] (14H,4CH$_3$,CH$_2$); 2.08–2.45 (m,4H,2CH$_2$); 2.55–3.65 (m,6H,2CH$_2$,CHCH), 5.62–5.82 (m,2H,CH=CH); 6.32 (s,1H,CH=) (D$_2$O) |
| 67. | C$_{19}$H$_{25}$N$_3$O$_4$ (359.45) | 63.49 / 63.38 | 7.01 / 7.00 | 11.69 / 11.54 | | | 1.52 (s,6H,2CH$_3$); 1.62 (s,6H,2CH$_3$); 3.35–3.55 (m,4H,CH$_2$CH$_2$); 6.34 (s,1H, CH=); 7.28–7.56 (m,4H.ArCH=) (D$_2$O) |
| 68. | C$_{20}$H$_{27}$N$_3$O$_4$ (373.47) | 64.33 / 64.25 | 7.29 / 7.28 | 11.25 / 11.29 | (14H,4CH$_3$,CH$_2$); 3.05–3.80 (m,4H,2CH$_2$); | | [1.52 (s), 1.62 (s),1.35–2.05 (m)] 6.20 (s,1H,CH=); 7.25–7.55 (m,4H, ArCH=)$_2$(D$_2$O) |
| 69. | C$_{20}$H$_{26}$N$_4$O$_2$. 2HCl (427.40) | 56.21 / 56.12 | 6.60 / 6.41 | 13.11 / 13.20 | 16.59 / 16.81 | | 1.40 (s,6H,2CH$_3$); 1.54 (s,6H,2CH$_3$); 3.00 (s,3H,CH$_3$); 3.40–3.85 (m,4H, 2CH$_2$); 6.32 (s,1H,CH=); 7.50.8.45 (m,4H,ArCH=) (D$_2$O) |
| 70. | C$_{21}$H$_{26}$N$_4$O$_2$. 2HCl (441.41) | 57.14 / 57.04 | 6.85 / 6.95 | 12.69 / 12.75 | 16.06 / 16.07 | 1.70–2.40 (m,2H,CH$_2$); 3.00 (s,3H, CH$_3$); | 1.60 (s,6H,2CH$_3$); 1.70 (s,6H,2CH$_3$); 3.20–3.84 (m,2H,CH$_2$); 4.10–4.45 (m,2H,CH$_2$); 6.34 (s,1H.CH=); 7.54–8.45 (m,4H,ArCH=) (D$_2$O) |
| 71. | C$_{21}$H$_{28}$N$_4$O$_2$. | 62.29 | 7.22 | 13.84 | 8.75 | | 1.10–1.62 (m,3H,CH$_3$); 1.32 (s,6H, |

TABLE I-continued $R^1-CONH-A-R^2$

| | | | | | | |
|---|---|---|---|---|---|---|
| HCl (404.94) | | 62.11 | 7.38 | 14.04 | 9.06 | 2CH$_3$); 1.50 (s,6H,2CH$_3$); 2.50–3.15 3.35–3.74 (m,2H,CH$_2$); 4.02–4.40 (m,2H,CH$_2$); 6.20 (s,1H,CH=); 7.20–8.05 (m,4H,ArCH=) (D$_2$O) |
| 72. | C$_{22}$H$_{30}$N$_4$O$_2$· | 58.02 | 7.08 | 12.30 | 15.57 | 1.30–1.58 (m,3H,C-H$_3$); 1.52 (s,6H, |
| | 2HCl | 56.92 | 7.30 | 12.54 | 15.68 | 2CH$_3$); 1.62 (s,6H,2C-H$_3$); 1.70–2.44 |
| | (455.44) | | | | | (m,2H,CH$_2$); 3.00–3.66 (m,4H,2CH$_2$); 4.08–4.54 (m,2H,CH$_2$); 6.34 (s,1H, CH=); 7.45–8.55 (m,4H,ArCH=) (D$_2$O) |
| 73. | C$_{21}$H$_{30}$N$_4$OP$_2$·2HCl (443.43) | 56.88 56.92 | 7.28 7.30 | 12.64 12.56 | 15.99 16.07 | 1.30–1.55 (m,12H,4CH$_3$); 2.25–2.55 (m,2H,CH$_2$); 2.92 (s,3H,CH$_3$); 3.05–3.55 (m,5H,2CH$_2$,CH); 3.95–4.55 (m, 2H,CH$_2$); 7.50–8.30 (m,4H,ArCH=) (D$_2$O) |
| 74. | C$_{22}$H$_{32}$N$_4$O$_2$· 2HCl (457.47) | 57.77 57.89 | 7.49 7.61 | 12.25 12.33 | 15.50 15.47 | 1.25–1.70 (m,15H,5CH$_3$); 1.75–2.45 (m,4H,2CH$_2$); 2.95–3.70 (m,5H,2CH$_2$,CH) 3.90–4.45 (m,2H,CH$_2$); 7.45–8.25 (m, 4H,ArCH=) (D$_2$O) |
| 75. | C$_{21}$H$_{28}$N$_4$O$_3$· 2HCl (457.41) | 55.14 55.26 | 6.61 6.72 | 12.25 12.37 | 15.50 15.73 | 1.58 (s,6H,2CH$_3$); 1.68 (s,6H,2CH$_3$); 2.96 (s,3H,CH$_3$); 3.25–3.70 (m,2H, CH$_2$); 3.90–4.50 (m,3H,CH$_2$CH); 6.38 (s,1H,CH=); 7.45–8.35 (m,4H,ArCH=) (D$_2$O) |

TABLE II

| Substance No. | Dose mg./kg. i.v. | n | positive cases % | arrhythmia appearance time min. ± S.E. | ED$_{125}$ mg/kg i.v. | ED$_{150}$ mg/kg i.v. | LD$_{50}$ mg/kg i.v. |
|---|---|---|---|---|---|---|---|
| Antiarrhythmic activity and acute toxicity of the compounds of the general formula IA | | | | | | | |
| I/44 | 6.5 | 10 | 100 | 30 | 3.6 (3.1–4.2) | 5.3 (4.6–6.1) | 65 (60–68) |
| I/50 | 4.3 | 10 | 100 | 30 | 2.7 (2.3–3.2) | 4.2 (3.6–5.0) | 43 (36–52) |
| I/36 | 4.0 | 10 | 70 | 15.9 ± 0.3 | 4.5 (3.4–5.7) | 7.6 (6.4–8.7) | 49 (44–55) |
| I/49 | 2.8 | 10 | 90 | 10.0 | 2.3 (1.8–3.0) | 4.7 (3.6–6.2) | 28 (23–35) |
| I/38 | 4.0 | 10 | 90 | 27.5 | 2.2 (1.7–2.8) | 3.6 (3.1–4.2) | 26 (19–35) |
| I/52 | 4.0 | 10 | 90 | 7.3 | 2.1 (1.8–2.4) | 2.9 (2.6–3.4) | 39 (31–50) |
| I/53 | 4.0 | 10 | 100 | 30 | 3.4 (2.8–4.1) | 5.5 (4.6–6.6) | 28 (24–33) |
| I/54 | 4.0 | 10 | 70 | 5.2 ± 0.8 | 6.9 (5.5–8.9) | 13.2 (10.4–16.8) | 19 (15–24) |
| procainamide | 8.0 | 10 | 30 | 9.5 ± 1.2 | 11.0 (9.6–12.2) | 14.0 (13.0–15.1) | 141 (132–151) |
| quinidine | 9.5 | 10 | 70 | 10.0 ± 0.4 | 7.8 (6.7–8.6) | 10.8 (9.6–12.1) | 95 (78–118) |
| Antiarrhythmic activity and acute toxicity of the compounds of the general Formula IB | | | | | | | |
| I/11 | 1.4 | 10 | 80 | 20.1 ± 2.5 | 1.4 (1.1–1.7) | 2.4 (1.9–2.9) | 14 (13–16) |
| I/8 | 3.0 | 10 | 100 | >30 | 1.5 (1.2–1.7) | 2.2 (1.9–2.6) | 30 (28–33) |
| I/9 | 1.9 | 10 | 100 | >30 | 0.7 (0.5–0.9) | 1.4 (1.1–1.9) | 19 (12–28) |
| I/19 | 7.0 | 10 | 80 | 27.5 ± 2.5 | 2.0 (1.7–2.4) | 3.1 (2.6–3.6) | 71 (59–86) |
| I/2 | 12.0 | 10 | 70 | 16.7 ± 1.7 | 7.6 (6.4–9.3) | 12.3 (10.2–14.7) | 119 (104–138) |
| I/21 | 4.0 | 10 | 100 | >30 | 2.4 (1.9–2.9) | 4.1 (3.4–5.0) | 18 (14–22) |
| I/12 | 4.0 | 10 | 90 | 28.5 | 4.6 (3.94–5.4) | 6.95 (5.9–8.1) | 38 (35–43) |
| I/22 | 4.0 | 10 | 100 | >30 | 1.9 (1.8–2.3) | 2.7 (2.4–3.0) | 14 (11–17) |
| quinidine | 9.5 | 10 | 70 | 10.0 ± 0.4 | 7.8 (6.7–8.6) | 10.8 (9.6–12.1) | 95 (78–118) |
| procainamide | 8.0 | 10 | 30 | 9.5 ± 1.2 | 11.0 (9.6–12.2) | 14.0 (13.0–15.1) | 141 (132–151) |
| Antiarrhythmic activity and acute toxicity of the compounds of the general Formula IC | | | | | | | |

TABLE II-continued

| Substance No. | Dose mg./kg. i.v. | n | positive cases % | arrhythmia appearance time min. ± S.E. | $ED_{125}$ mg/kg i.v. | $ED_{150}$ mg/kg i.v. | $LD_{50}$ mg/kg i.v. |
|---|---|---|---|---|---|---|---|
| I/59 | 5.5 | 10 | 100 | 30 | 4.2 (3.3–5.3) | 7.9 (6.2–10.2) | 55 (53–57) |
| I/60 | 2.3 | 10 | 90 | 26.0 | 1.4 (1.0–1.7) | 2.6 (2.0–3.0) | 23 (18–28) |
| I/68 | 41.9 | 10 | 40 | 4.6 ± 0.7 | — | — | 419 (403–438) |
| I/58 | 11.3 | 10 | 50 | 13.1 ± 2.5 | — | — | 113 (99–129) |
| I/61 | 4.0 | 10 | 100 | 30 | 1.9 (1.6–2.3) | 3.0 (2.6–3.6) | 28 (26–30) |
| I/62 | 4.0 | 10 | 100 | 30 | 2.6 (2.1–3.2) | 4.5 (3.7–5.5) | 22 (17–28) |
|  | 4.2 | 10 | 40 | (4.8 ± 0.9) | — | — | 42 (36–48) |
| quinidine | 9.5 | 10 | 70 | 10.0 ± 0.4 | 7.8 (6.7–8.6) | 10.8 (9.6–12.1) | 95 (78–118) |
| procainamide | 8.0 | 10 | 40 | 9.5 ± 1.2 | 11.0 (9.6–12.2) | 14.0 (13.0–15.1) | 141 (132–151) |
| I/70 | 4.0 | 10 | 100 | 30 | 2.5 (1.9–3.1) | 4.5 (3.6–5.7) | 31 (22–45) |
| I/71 | 4.0 | 10 | 100 | 30 | 3.8 (2.6–5.6) | 10.5 (7.1–15.4) | 48 (46–49) |
| I/72 | 4.0 | 10 | 100 | 30 | 1.1 (0.9–1.3) | 1.7 (1.4–1.9) | 13 (10–17) |
| I/74 | 4.0 | 10 | 100 | 30 | 1.9 (1.7–2.2) | 2.7 (2.4–3.1) | 22 (18–26) |
|  |  |  |  |  | — | — | 42 (36–48) |
| quinidine | 9.5 | 10 | 70 | 10.0 ± 0.4 | 7.8 (6.7–8.6) | 10.8 (9.6–12.1) | 95 (78–118) |
| procainamide | 8.0 | 10 | 30 | 9.5 ± 1.2 | 11.0 (9.6–12.2) | 14.0 (13.0–15.1) | 141 (132–151) |

TABLE III

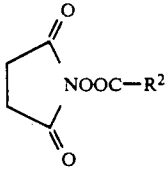

| No | $R^2$ | m.p. °C. | Molecular formula | C | H | N | S | $^1$H-NMR δ (ppm) |
|---|---|---|---|---|---|---|---|---|
| 1. | 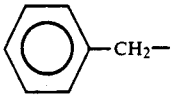 | 112–114 | $C_{12}H_{11}NO_4$ (233.24) | 61.80 62.04 | 4.75 4.99 | 6.01 6.20 |  | 2.70(s, 4H, 2CH$_2$); 3.90 (s, 2H, CH$_2$); 7.30(s, 5H, ArCH=)(CDCl$_3$) |
| 2. | 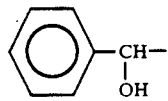 | 115–116 | $C_{12}H_{11}NO_5$ (249.23) | 57.83 57.64 | 4.45 4.52 | 5.62 5.88 |  | 2.82(s, 4H, 2CH$_2$); 5.60 (d, 1H, CH); 6.70(d, 1H, OH); 7.30–7.60(m, 5H, ArCH=)(DMSO-d$_6$) |
| 3. | 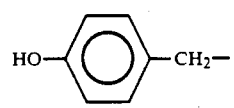 | 133–134 | $C_{12}H_{11}NO_5$ (249.23) | 57.83 57.59 | 4.45 4.32 | 5.62 5.68 |  | 2.80(s, 4H, 2CH$_2$); 3.84 (s, 2H, CH$_2$); 6.70–7.40 (s, 5H, ArCH=)(CDCl$_3$) |
| 4. | 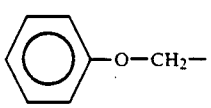 | 99–100 | $C_{12}H_{11}NO_5$ (249.23) | 57.83 58.02 | 4.45 4.53 | 5.62 5.84 |  | 2.78(s, 4H, 2CH$_2$); 4.92 (s, 2H, CH$_2$); 6.80–7.50 (m, 5H, ArCH=)(CDCl$_3$) |

TABLE III-continued

| No | R² | Starting materials m.p. °C. | Molecular formula | Analyses, % calcd/found C | H | N | S | ¹H-NMR δ (ppm) |
|---|---|---|---|---|---|---|---|---|
| 5. | CH₂=CH–CH₂–(Ar with OCH₃)–O–CH₂– | 98–99 | $C_{16}H_{17}NO_6$ (319.33) | 60.19 / 60.25 | 5.37 / 5.49 | 4.39 / 4.61 | | 2.80(s, 4H, 2CH₂); 3.30 (d, 2H, =CH₂); 3,82(s, 3H, OCH₃); 4.95(s, 2H, OCH₂); 5.05–5.30(m, 2H, CH₂); 5.50–6.35(m, 1H, CH=); 6.50–7.00(m, 3H, ArCH=)(CDCl₃) |
| 6. | CH₃–CH=CH–(Ar with OCH₃)–O–CH₂– | 142–144 | $C_{16}H_{17}NO_6$ (319.33) | 60.19 / 60.33 | 5.37 / 5.45 | 4.39 / 4.37 | | 1.85(d, 3H, CH₃); 2.80 (s, 4H, 2CH₂); 3.85(s, 3H, OCH₃); 4.96(s, 2H, OCH₂); 5.82–6.55(m, 2H, CH=CH); 6.85(s, 3H, ArCH=)(CDCl₃) |
| 7. | H₃C–(Ar)(CH₂–CH=CH₂)–O–CH₂– | 81–82 | $C_{16}H_{17}NO_5$ (303.33) | 63.36 / 63.52 | 5.65 / 5.77 | 4.62 / 4.59 | | 2.25(s, 3H, CH₃); 2.80(s, 4H, 2CH₂); 3.38(d, 2H, =CH₂); 4.94(s, 2H, OCH₂); 5.02–5.32(m, 2H, CH₂); 5.50–6.42(m, 1H, CH=); 6.50–7.02(m, 3H, ArCH=)(CDCl₃) |
| 8. | Ph–S–CH₂ | 97–98 | $C_{12}H_{11}NO_4S$ (265.30) | 54.33 / 54.43 | 4.18 / 4.33 | 5.28 / 5.19 | 12.09 / 12.11 | 2.84(s, 4H, 2CH₂); 3.94 (s, 2H, SCH₂); 7.04–7.55 (m, 5H, ArCH=)(DMSO-d₆) |
| 9. | 2-thienyl | 159–161 | $C_9H_7NO_4S$ (225.23) | 48.00 / 47.81 | 3.13 / 2.93 | 6.22 / 6.05 | 14.24 / 14.11 | 2.92(s, 4H, 2CH₂); 7.20–7.52(m, 1H, CH=); 8.00–8.35(m, 2H, 2CH=) (DMSO-d₆) |
| 10. | 2-thienyl–CH₂– | 128–130 | $C_{10}H_9NO_4S$ (239.26) | 50.21 / 50.33 | 3.79 / 4.00 | 5.85 / 5.79 | 13.40 / 13.22 | 2.80(s, 4H, 2CH₂); 4.34 (s, 2H, CH₂); 6.90–7.52 (m, 3H, 3CH=) (DMSO-d₆) |

$$\text{N–OOC–R}^2 \text{ (succinimide ester)}$$

| No | R² | m.p. °C. | Molecular formula | C | H | N | S | ¹H-NMR δ (ppm) |
|---|---|---|---|---|---|---|---|---|
| 11. | Cl–(Ar)–O–C(CH₃)₂– | 111–112 | $C_{14}H_{14}ClNO_5$ (311.72) | 53.94 / 53.74 | 4.54 / 4.39 | 4.49 / 4.26 | | 1.70(s, 6H, 2CH₃); 2.80 (s, 4H, CH₂CH₂); 6.80–7.40 (s, 4H, ArCH=) |
| 12. | 2,4-Cl₂–(Ar)–O–CH₂– | 85–86 | $C_{12}H_9Cl_2NO_5$ (318.12) | 45.31 / 45.28 | 2.85 / 3.09 | 4.40 / 4.37 | | 2.84(s, 4H, CH₂CH₂); 5.14(s, 2H, OCH₂); 6.80–7.40(m, 3H, ArCH=) |
| 13. | Cl–(Ar)(CH₃)–O–CH₂– | | $C_{13}H_{12}ClNO_2$ (297.70) | 52.45 / 52.69 | 4.06 / 3.93 | 4.71 / 4.70 | | 2.28(s, 3H, CH₃); 2.82 (s, 4H, CH₂CH₂); 4.96 (s, 2H, OCH₂); 6.40–7.30 (m, 3H, ArCH=) |

TABLE III-continued

| No | R² | m.p. °C. | Molecular formula | Analyses, % calcd/found | | | | ¹H-NMR δ (ppm) |
|---|---|---|---|---|---|---|---|---|
| | | | | C | H | N | S | |
| 14 | ![structure: 2,6-dimethylphenoxy with CH(CH₃)] | 85–86 | $C_{15}H_{17}NO_3$ (259.32) | 69.48 69.72 | 6.61 6.84 | 5.40 5.43 | | 1.70(d, 3H, CH₃); 2.30 (s, 6H, 2CH₃); 2.74(s, 4H, CH₂CH₂); 4.26(t, 1H, CH); 6.44(s, 3H, ArCH=) |
| 15. | ![structure: CH₃-HC=HC-phenyl-OCH₃ with O-CH(CH₃)] | 115–116 | $C_{17}H_{19}NO_5$ (333.35) | 61.25 61.11 | 5.74 5.53 | 4.20 4.31 | | 1.70–1.90(m, 6H, C—CH₃, =C—CH₃); 2.74(s, 4H, CH₂CH₂); 3.84(s, 3H, OCH₃); 4.57(t, 1H, CH); 5.50–7.20(m, 5H, CH=CH, ArCH=) |
| 16. | ![structure: CH₃O-phenyl-CH₂-CH=CH₂ with O-CH₂-COO-tetrachlorophenyl] | 108–110 | $C_{18}H_{13}Cl_5O_4$ (470.57) | 45.94 45.85 | 2.78 3.08 | — | | 3.30(d, 2H, =CH₂); 3.85 (s, 3H, OCH₃); 5.02(s, 2H, OCH₂); 5.05–5.25(m, 1H, CH); 6.50–6.90(m, 3H, ArCH=) |

What is claimed is:

1. A compound of the Formula (I)

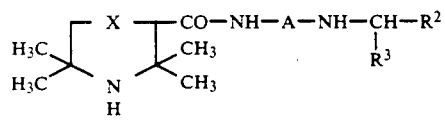

wherein
A is $C_1$ to $C_5$ alkylene which can be substituted by hydroxyl;
X is a single chemical bond or a double bond;
R² is phenyl, thienyl, or pyridyl each unsubstituted or substituted by one or two or three substituents selected from the group consisting of halogen, $C_1$ to $C_4$ alkoxy, acetylamino, or trifluoromethyl; and
R³ is hydrogen or $C_1$ or $C_4$ aklyl; or a pharmaceutically acceptable acid addition salt thereof.

2. An antiarrhythmic pharmaceutical composition which comprises a pharmacologically effective amount of the compound of the Formula (I) as defined in claim 1, or a pharmaceutically acceptable acid addition salt thereof in combination with a pharmaceutically acceptable inert carrier.

3. A method of treating arrhythmia in an animal subject which comprises the step of administering to said subject in need of antiarrhythmic treatment, a therapeutically effective amount of the compound of the Formula (I) defined in claim 1 or a pharmaceutically acceptable acid addition salt thereof.